United States Patent
Machamer et al.

(10) Patent No.: US 11,844,554 B1
(45) Date of Patent: Dec. 19, 2023

(54) RETROGRADE FEMORAL NAIL SYSTEM AND RELATED METHODS

(71) Applicant: GLOBUS MEDICAL, INC., Audubon, PA (US)

(72) Inventors: David Machamer, Glen Mills, PA (US); Nathaniel Yuchimiuk, Sanatoga, PA (US); Jonan A. Philip, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/815,751

(22) Filed: Jul. 28, 2022

(51) Int. Cl.
*A61B 17/72* (2006.01)
*A61B 17/17* (2006.01)

(52) U.S. Cl.
CPC ...... *A61B 17/7241* (2013.01); *A61B 17/1717* (2013.01); *A61B 17/7225* (2013.01)

(58) Field of Classification Search
CPC ........ A61B 17/7233–725; A61B 17/72; A61B 17/17
See application file for complete search history.

(56) References Cited

U.S. PATENT DOCUMENTS

| | | | | |
|---|---|---|---|---|
| 10,722,269 B2 * | 7/2020 | Cowens | ............ | A61B 17/8605 |
| 2007/0276382 A1 * | 11/2007 | Mikhail | ............ | A61B 17/7225 606/62 |
| 2011/0245885 A1 * | 10/2011 | Powell | ............... | A61B 17/1725 606/86 R |
| 2011/0282347 A1 * | 11/2011 | Gordon | .............. | A61B 17/1725 606/104 |
| 2013/0172890 A1 * | 7/2013 | Limouze | ............ | A61B 17/1675 606/62 |
| 2015/0305791 A1 * | 10/2015 | Purohit | .............. | A61B 17/1707 606/96 |
| 2018/0140310 A1 * | 5/2018 | Machamer | ......... | A61B 17/1725 |
| 2021/0153919 A1 * | 5/2021 | Schumacher | ........ | A61B 17/921 |
| 2021/0338293 A1 * | 11/2021 | Silva | ................... | A61B 17/8052 |

\* cited by examiner

*Primary Examiner* — Eduardo C Robert
*Assistant Examiner* — Michelle C Eckman

(57) ABSTRACT

Described herein are retrograde femoral nails and insertion systems suitable for stabilizing femoral fractures of the shaft and femur. After reaming the femoral canal, the intramedullary nail may be inserted with a retrograde approach through the knee. The nail includes four-start threaded holes in the distal region. The nail also includes oblique distal holes with a trajectory that targets the bone in the posterior condyles. The insertion instrumentation assembly and system includes an insertion handle with a retaining thread that prevents the connection bolt from falling out. An assembly shaft is also included, which assists the user in connecting the nail to the insertion handle. The system further includes an aiming guide with a retention mechanism that holds driver sleeves in place. The aiming guide also contains a hole to position a locking washer holder to interface with the nail.

14 Claims, 21 Drawing Sheets

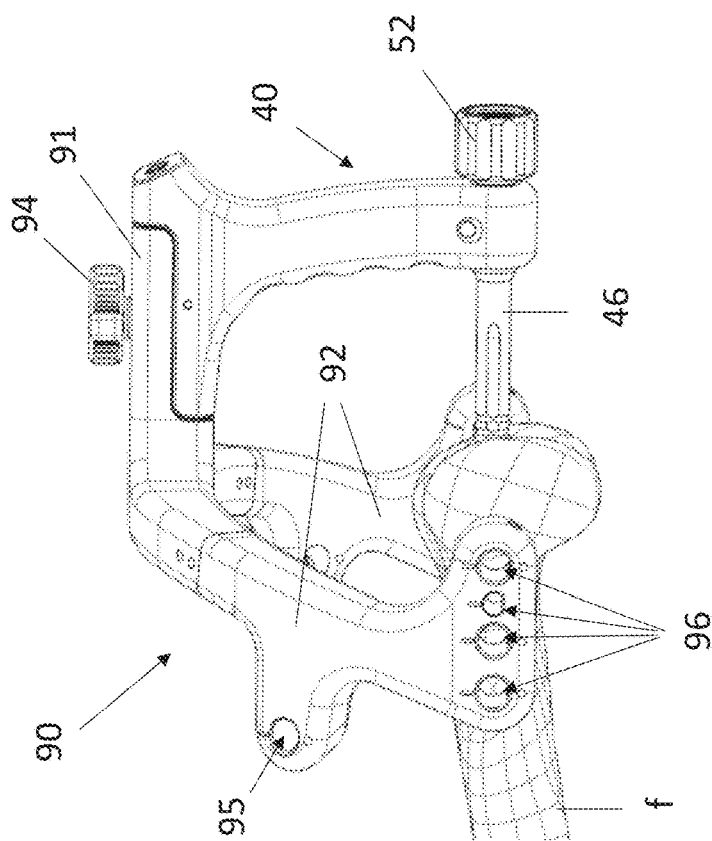
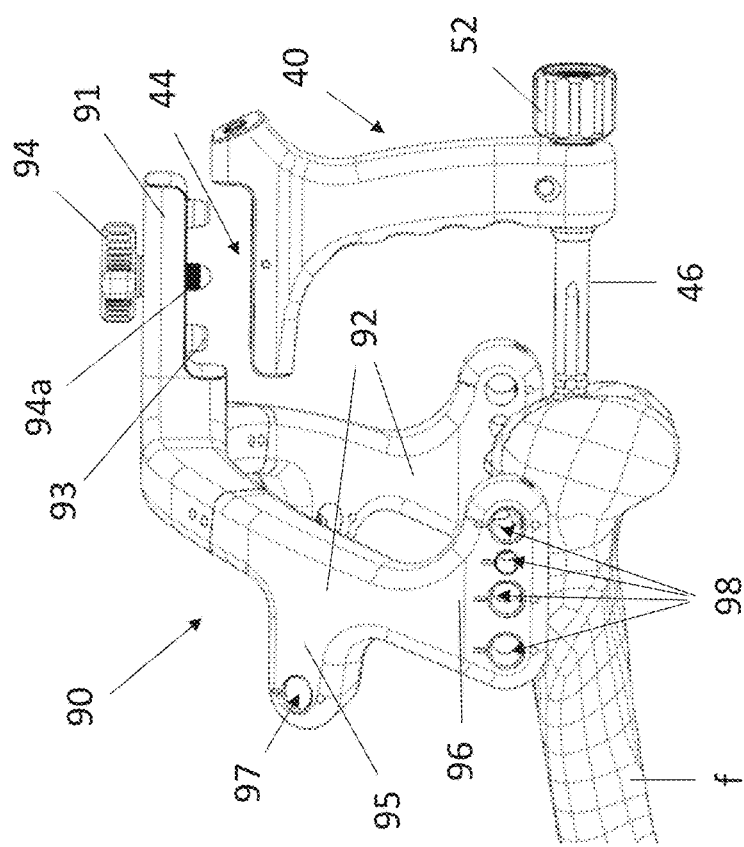

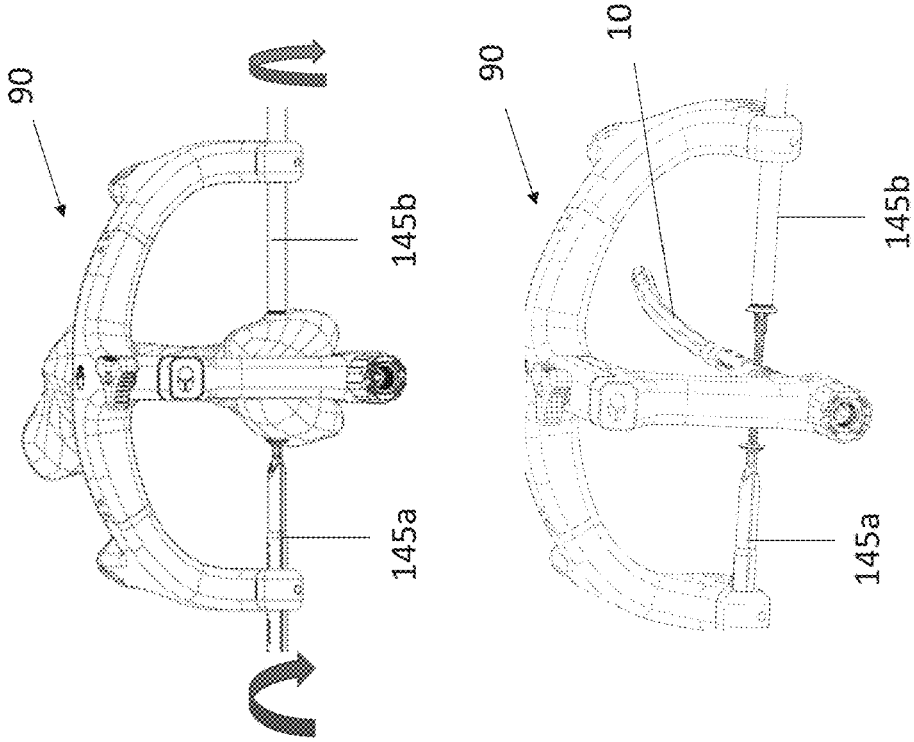
FIG. 13D
FIG. 13E
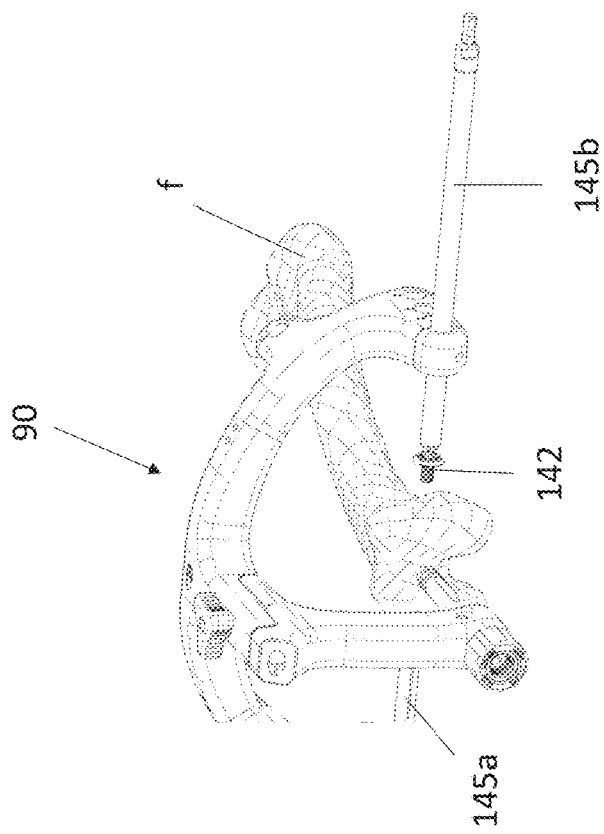
FIG. 13C

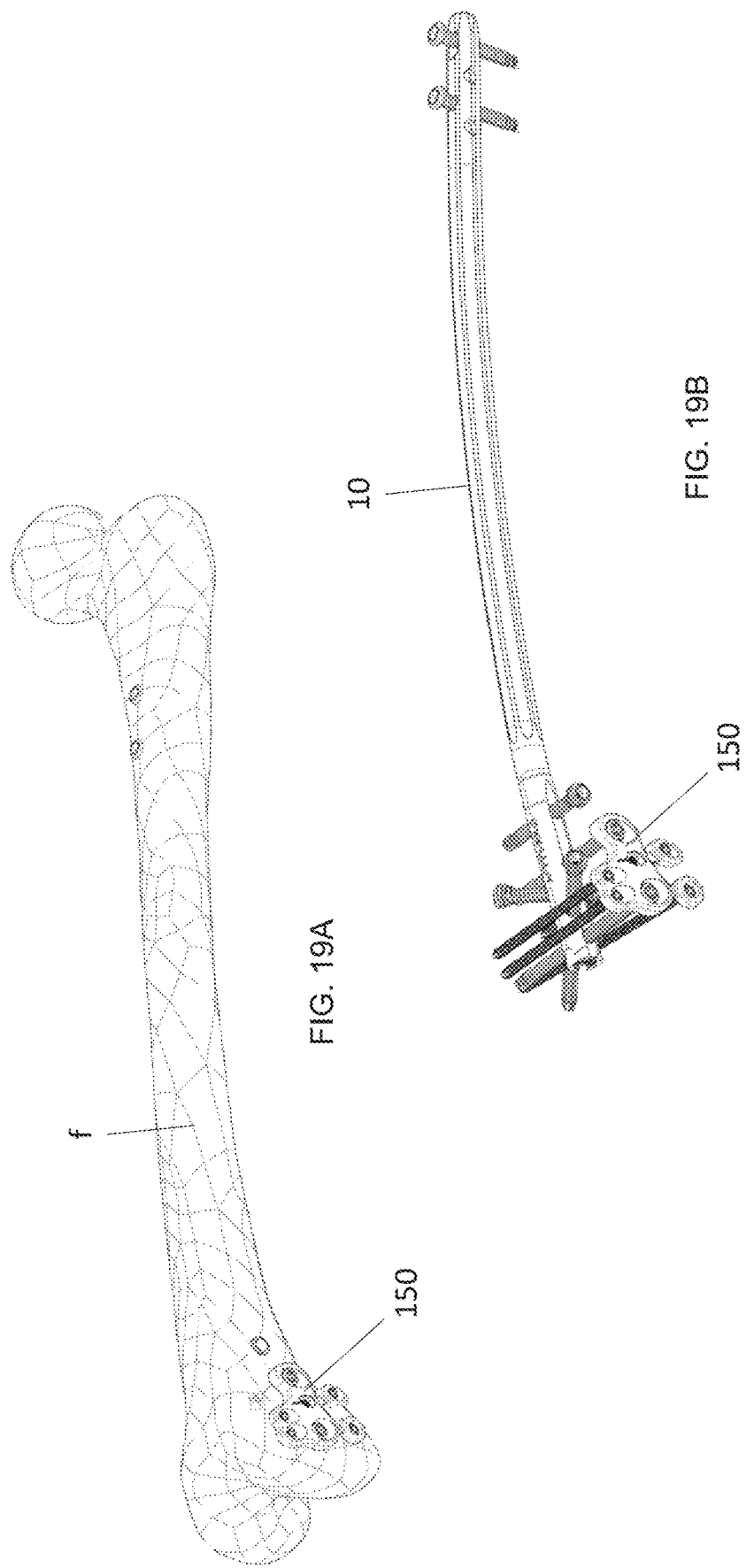

RETROGRADE FEMORAL NAIL SYSTEM AND RELATED METHODS

FIELD

The present disclosure generally relates to intramedullary nails and associated insertion instruments for treating bone fractures.

BACKGROUND

Following an injury to a long bone, such as one or multiple fractures of the femur, fixation devices are often used to immobilize the fracture fragments and stabilize the long bone. Intramedullary nails, for example, may be inserted into the intramedullary or femoral canal and provide the appropriate proximal and/or distal fixation. However, known intramedullary devices can suffer from a number of disadvantages. For example, the nail may lack the necessary locking screw receiving engagements or lack the proper trajectories for screw engagement. In other instances, the nail may be susceptible to implant failure due to difficulties or inefficiencies in positioning of the nail within the bone. Further still, there may be difficulties in alignment of fixation screws with respect to the implanted intramedullary nail. Thus, there is a need in the art for an improved femoral nail and insertion instruments used in the treatment of bone fractures and bone stabilization. The present invention satisfies this need.

BRIEF SUMMARY

An intramedullary nail is described. The nail includes an elongate body having a proximal end, a distal end, and a cannulation from the distal end into a distal region of the elongate body. The opening at the distal end of the cannulation is threaded. The nail includes a first set of threaded transverse openings each passing through the elongate body in the distal region, where at least one of the threaded transverse openings is a four-start threaded opening. The nail also includes a second set of transverse openings passing through the elongate body in a proximal region of the elongate body. In some embodiments, at least one of the first set of threaded transverse openings is positioned 54 mm from the distal end of the elongate body. In some embodiments, at least one of the first set of threaded transverse openings is positioned 8 mm from the distal end of the elongate body. In some embodiments, at least one of the first set of threaded transverse openings is at an oblique angle from a longitudinal axis of the elongate body. In some embodiments, the oblique angle opening is configured to have a trajectory towards a posterior condyle of a femur when the nail is positioned within the intramedullary canal of the femur. In some embodiments, the nail has a proximal bend of 5° to 10°. In some embodiments, the nail has a radius of curvature extending to the proximal end of the elongate body. In some embodiments, the proximal bend begins proximally from the distal region of the elongate body. In some embodiments, the distal region of the elongate body has a larger cross-sectional diameter than the remainder of the elongate body. In some embodiments, the second set of transverse openings includes one slotted opening and three threaded openings.

Also described is an intramedullary nail insertion system. The system includes an insertion handle having a front surface and a back surface. The system also includes a hollow extension shaft having a threaded distal end opening and a proximal end opening, the distal end initiating from the back surface of the handle and the proximal end extending outward from the front surface of the insertion handle, thereby forming a channel from the back surface of the handle to the proximal end of the extension shaft. The extension shaft channel includes a cavity portion proximal to the distal threaded end opening. The system also includes a hollow connection bolt having a distal end and a threaded proximal end and a length therebetween. The connection bolt is sized to fit within the hollow extension shaft, and includes a threaded region on an outside surface along its length and sized to engage the threading of the distal end opening of the extension shaft. The cavity portion of the extension shaft has a diameter equal to or greater than the outer diameter of the connection bolt outer threading, and the portion of the extension shaft channel proximal to the cavity has a diameter that is smaller than the outer diameter of the connection bolt outer threading. The system also includes an aiming guide having two opposing arcuate guide arms and a connection arm, where the connection arm releasably engages the insertion handle, and each guiding arm includes one or more guide holes. In some embodiments, the threaded proximal end of the connection bolt extends beyond the proximal end of the extension shaft and is sized to engage and secure a threaded distal end of an intramedullary nail. In some embodiments, the system further includes an insertion assembly shaft having a distal end and a proximal end and a length therebetween, where the assembly shaft length fits within the hollow interior of the connection bolt, and where the assembly shaft length is greater than the length of the connection bolt, such that the proximal end of the assembly shaft is extendable into a distal end cannulation of the intramedullary nail when the nail is engaged with the connection bolt. In some embodiments, one or more of the guide holes of the aiming guide are aligned with one or more distal end openings of the intramedullary nail when the nail is engaged with the connection bolt. In some embodiments, the system includes a driver sleeve sized to fit within the one or more guide holes of the aiming guide. In some embodiments, the system includes a driver sleeve retention mechanism, where the mechanism is configured to generate a frictional securement of the driver sleeve when the driver sleeve is inserted into the guide hole of the aiming guide and rotated radially. In some embodiments, the system includes a locking washer having one or more holes that align with both the one or more guide holes of the aiming guide and the one or more distal end openings of the intramedullary nail. In some embodiments, the aiming guide includes a washer mounting guide hole, and wherein the locking washer includes a mounting hole aligned with the washer mounting guide hole of the aiming guide. In some embodiments, the locking washer includes a precontoured region configured to match the surface of a target bone. In some embodiments, the locking washer includes a deformable region, wherein at least one hole is positioned within the deformable region.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIGS. 1A and 1B are alternative side views. FIGS. 1C and 1D are cross-sectional views on C-C and D-D, respectively. FIG. 1E is a close-up view of the distal end of the exemplary nail.

FIGS. 9A and 9B illustrate an exemplary aiming guide attachable to the insertion handle assembly.

FIGS. 13A-13E illustrate an exemplary placement of a locking screw and condyle nut into an intramedullary nail within bone.

FIGS. 19A and 19B illustrate an exemplary final construct with all insertion instrumentation removed, both with and without bone.

DETAILED DESCRIPTION

Figures 1A, 1B:
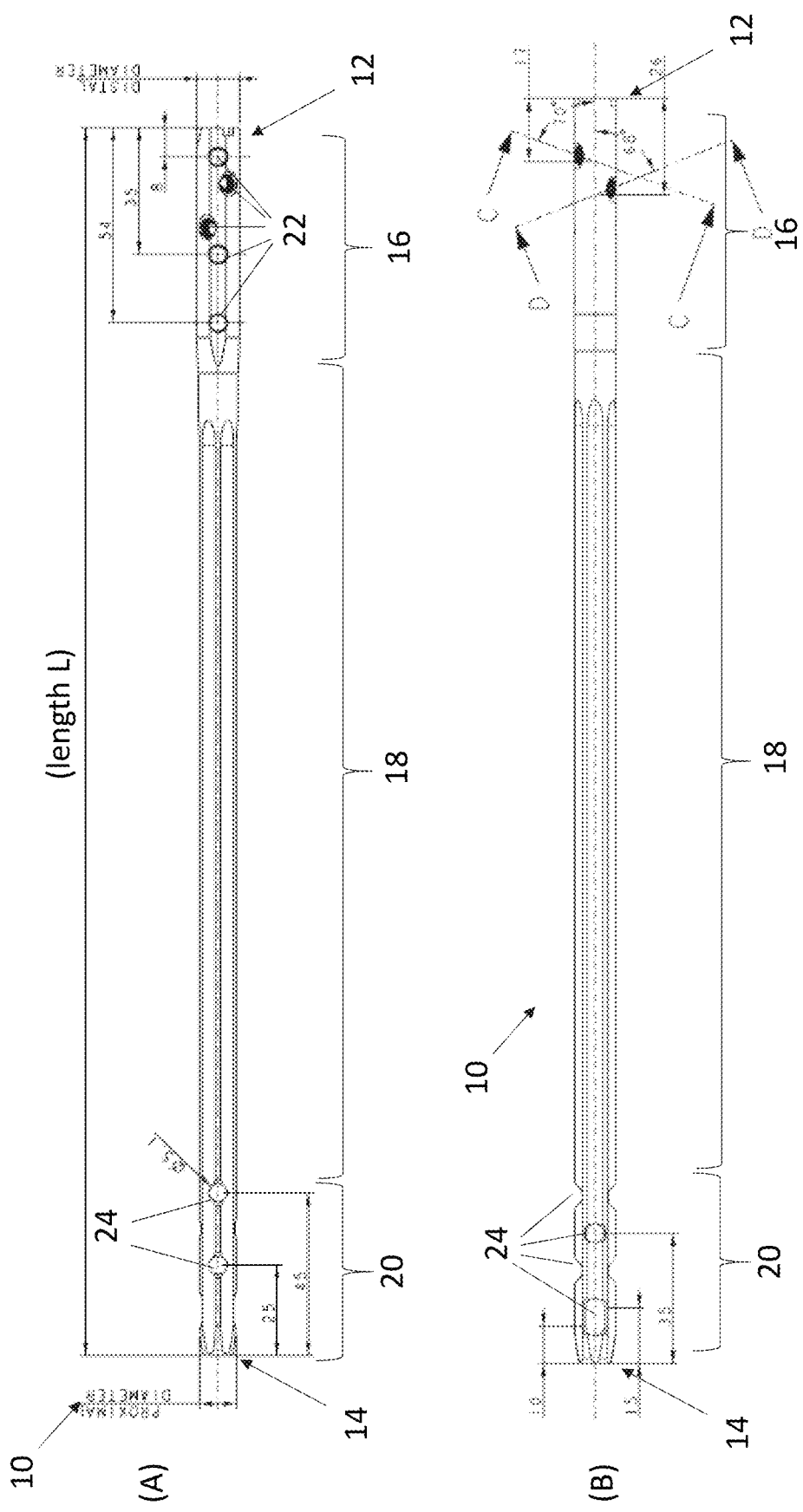
FIGS. 1A-1E illustrate an exemplary intramedullary nail in an unbent configuration.

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section. The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20%, ±10%, ±5%, ±1%, and ±0.1% from the specified value, as such variations are appropriate.

Reference herein to "one embodiment", "an embodiment" or "some embodiments" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Described herein are retrograde femoral nails suitable for stabilizing femoral fractures of the shaft and distal femur. After reaming the femoral canal, the intramedullary nail may be inserted with a retrograde approach through the knee. Although further described with reference to fractures of the femur, it should be appreciated that the intramedullary nail and insertion system may be adapted for use with any long bone.

As contemplated throughout the disclosure, the retrograde femoral nail has several features that are significant and unexpected improvements over the existing art. For example, and without limitation, the nail includes four-start threaded holes in the distal locations. These threaded holes create additional and significant stability through a fixed angle construct. In another example, the nail includes distal holes located at about 8 mm and about 54 mm from the distal end of the nail. These holes uniquely allow the nail to be used to treat femoral shaft fractures. In another example, the oblique distal holes of the nail are designed with a trajectory that targets the bone in the posterior condyles which is the strongest bone that provides the best screw purchase.

The insertion instrumentation assembly and system also contain several unique features that are significant improvements over the existing art. For example, the insertion handle has an ergonomic gripping surface for ease of use for the surgeon. In another example, the insertion handle also contains a retaining thread that prevents the connection bolt from falling out. In another example, the assembly shaft assists the user in connecting the nail to the insertion handle. In another example, the aiming guide contains a retention mechanism that holds the driver sleeve in place. In another example, the aiming guide also contains a hole to position the locking washer holder to interface with the nail.

Retrograde Femoral Nail

In a first aspect, the present invention includes a retrograde femoral nail, or intramedullary nail (referred to herein as a "nail"), suitable for stabilizing various types of femoral fractures. In some embodiments, the nail has five distal locking options, all with threaded holes for creating fixed angle constructs. In some embodiments, the nail can be used with 5 mm locking screws, locking washers, condyle nuts, and washers to stabilize the nail in the femoral canal and to resist axial and torsional forces. The locking washers are suitable for use in the femoral condyles for highly comminuted fractures, bone loss, and/or poor bone quality. In some embodiments, the locking washers are pre-contoured to fit the anatomy and may include polyaxial locking holes for 3.5 and 5.0 locking screws. In some embodiments, the locking washer also includes deformable tabs with 3.5 polyaxial locking holes that may be contoured in-situ for an ideal fit. The locking washer can be sized for a variety of lengths and hole configurations for treatment of different fracture types and locations. In some embodiments, the locking washers can be targeted using an aiming guide. In some embodiments, the condyle nuts and washers can be used to apply compression to the femoral condyles and to provide more surface area for compression in patients with poor bone quality. In some embodiments, the nail may be used in femoral fractures that include a knee joint replacement prosthesis. In some embodiments, the femoral nail may also be used along with a plate to stabilize femur fractures that extend into the articular surface of the knee. In some embodiments, the nail may have flats to allow insertion into knee replacements.

Referring now to FIGS. 1A and 1B, nail 10 (unbent configuration) includes a distal end 12, a proximal end 14 and a length L therebetween. The elongate body of nail 10 includes a generally defined distal region 16, central region 18, and proximal region 20. Nail 10 may be generally rod-like and/or tubular in shape, with cross-sectional shapes being circular, elliptical, oval or any other desirable geometry. Nail 10 may be hollow (e.g., having a channel therethrough) or solid along its length, or alternatively having some regions hollow while other regions are solid. Nail 10 may have a uniform cross-sectional diameter along its entire length, or it may include one or more regions having a variable cross-sectional diameter. For example, in some embodiments distal region 16 may have a larger cross-sectional diameter than central region 18 and proximal region 20. In such instances, the transition from the larger diameter distal region 16 may include a taper to the smaller diameter central region 18. In some embodiments and without limitation, nail 10 may have a length of between 160-500 mm and cross-sectional diameters of between 9-15 mm. In some embodiments, nail 10 has a cross-sectional diameter of 9 mm, 10 mm, 11 mm, 12 mm, 13 mm, 14 mm, or 15 mm. In some embodiments, nail 10 may include flutes. For example, flutes may be included for nails having a diameter of greater than 11 mm.

Nail 10 includes at least one proximal opening 24 that is sized, shaped and configured to receive any type of fastener, such as bone screws, bone anchors, or other fixation devices that extend transversely through the proximal region 20 of nail 10. Openings 24 may be any shape. In some embodiments, openings 24 may be a round opening and/or a slot-shaped opening. In some embodiments, openings 24 may be threaded (including multi-start thread), grooved, smooth, or any combination thereof for engaging or passage of a fastener. Nail 10 may include any number of proximal openings 24, such as 1, 2, 3, 4, 5, 6, 7, 8, 9 or 10 openings. The positioning of proximal openings 24 will depend on the number of openings to be fit within the proximal region 20 of nail 10. For example, openings 24 may pass through nail 10 transversely at various locations along nail 10 at any angle in the XYZ planes relative to the longitudinal axis of nail 10. For example and without limitation, proximal openings 24 may be positioned about 5 mm to about 50 mm from the proximal end 14 of nail 10 along its length. In some embodiments, the openings 24 may be centrally positioned about 5 mm, about 15 mm, about 25 mm, about 35 mm and about 45 mm from proximal end 14 of nail 10, with adjacent openings being positioned radially about 90° from each other. It should be appreciated that there is no limitation to the distance and angles at which each opening 24 may be positioned, including any oblique or obtuse angles desired. The trajectory of openings 24 may be any trajectory in the XYZ planes as desired.

Figures 1C, 1D, 1E:
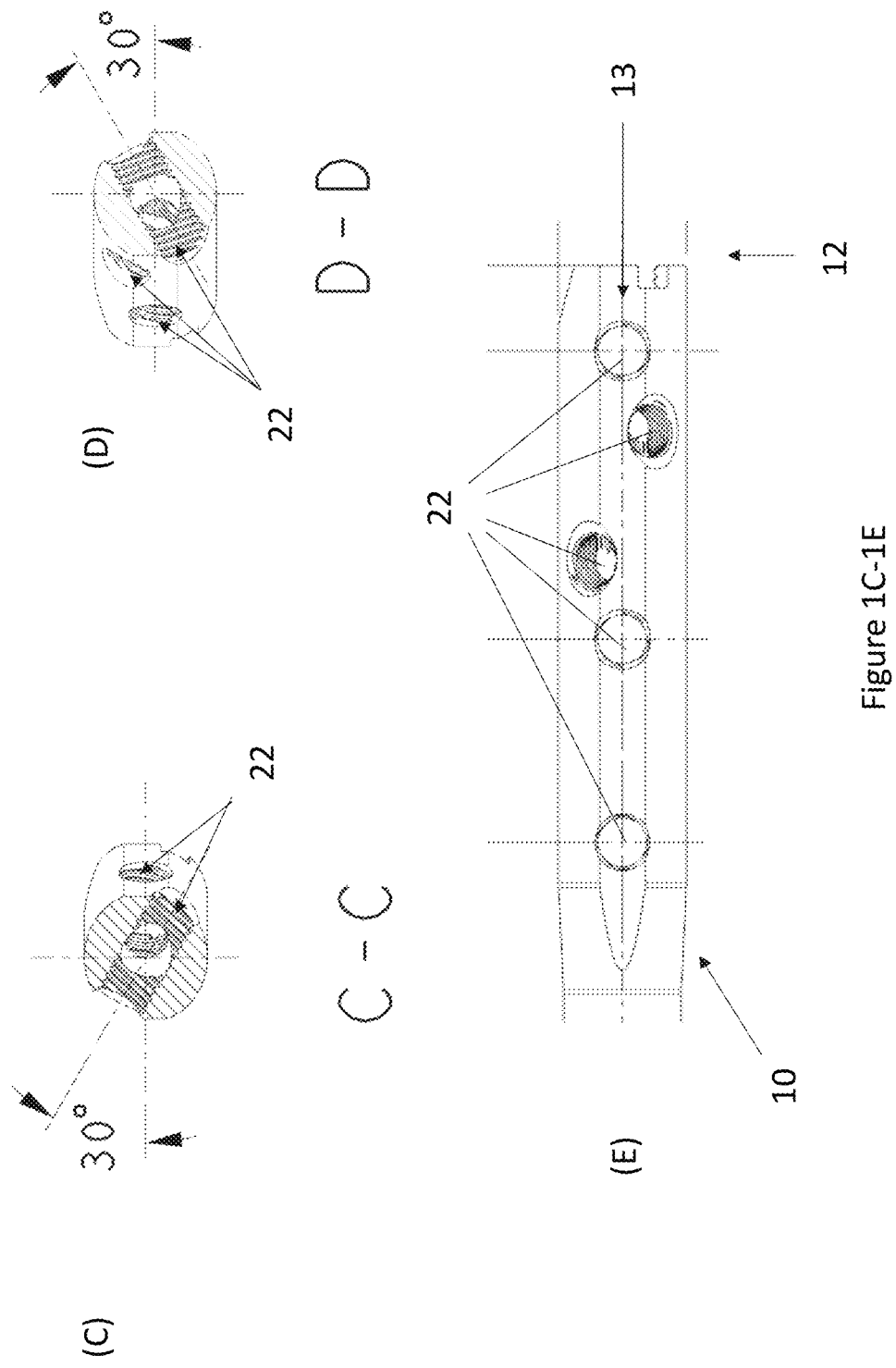

Nail 10 further includes at least one distal opening 22 that is also sized, shaped and configured to receive any type of fastener, such as bone screws, bone anchors, or other fixation devices that extend transversely through the distal region 16 of nail 10. Nail 10 may include any number of distal openings 22, such as 1, 2, 3, 4, 5, 6, 7, 8, 9 or 10 openings. The positioning of distal openings 22 will depend on the number of openings to be fit within the distal region 16 of nail 10. For example, openings 22 may pass through nail 10 transversely at various locations along nail 10 at any angle in the XYZ planes relative to the longitudinal axis of nail 10. For example and without limitation, distal openings 22 may be positioned about 5 mm to about 60 mm from the distal end 12 of nail 10 along its length. In some embodiments, the openings 22 may be centrally positioned about 5 mm, about 8 mm, about 15 mm, about 18 mm, about 25 mm, about 28 mm, about 35 mm, about 38 mm, about 45 mm, about 48 mm, and about 54 mm from distal end 12 of nail 10. In some embodiments and as shown in FIGS. 1C and 1D, openings 22 may be positioned with adjacent openings situated radially about 30° from each other. It should be appreciated that there is no limitation to the distance and angles at which each opening 22 may be positioned, including any right angles, oblique angles or obtuse angles desired. The trajectory of openings 22 may be any trajectory in the XYZ planes as desired. Openings 22 may be threaded, grooved, smooth, or any combination thereof. In some embodiments and as shown in FIG. 1E, openings 22 may be 4-start threaded openings. It should be appreciated that other multi-start threading may be used for any of openings 22 as desired. The distal end 12 of nail 10 may also be open, hollow or otherwise cannulated 13, and is further configured to engage components of one or more insertion instruments to assist in guiding and positioning nail 10 within a reamed intramedullary canal.

Figure 2:
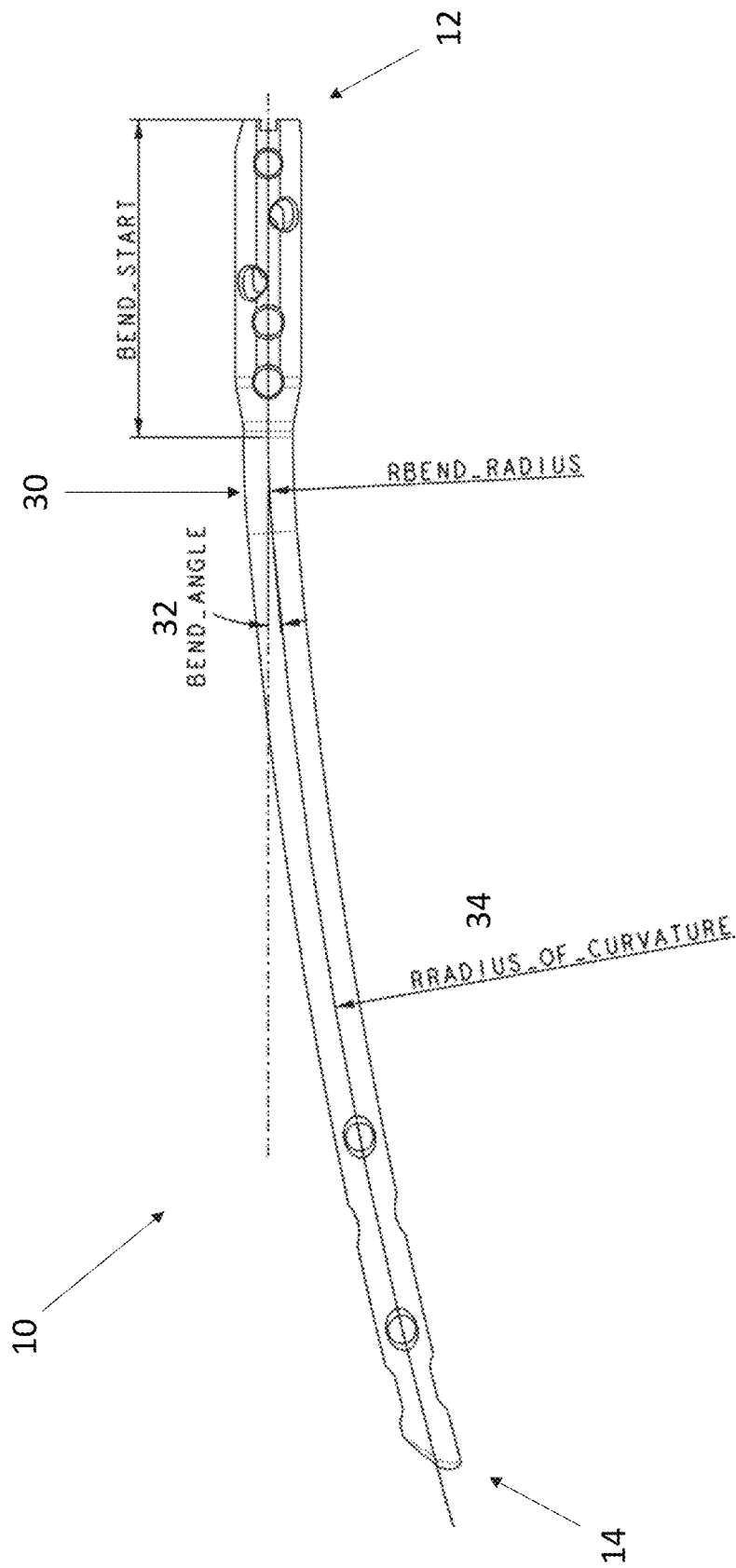
FIG. 2 illustrates another exemplary intramedullary nail having a bend and curvature along a portion of its length.

In some embodiments, the retrograde femoral nail includes a 5° or 10° proximal bend with a length dependent radius of curvature applied to the shaft of the nail. For example, nail 10 may further include a bend and/or radius of curvature along all or a portion of its length. As shown in FIG. 2, nail 10 may include a bend 30 initiating in the central region closest to distal region 16. In some embodiments, bend 30 begins between 54 mm and 94 mm from distal end 12 of nail 10. In some embodiments, the bend start may begin between 50 mm and 90 mm from the distal end of the nail, with a nominal value of about 70 mm. In some embodiments, the bend angle 32 may be between 0° and 20° with a nominal value of about 5°, 6°, 7°, 8°, 9° or 10°. In some embodiments, nail 10 may include a bend with a radius of curvature from the initial bend point to the proximal end 14 of nail 10. As contemplated herein, the bend radius can vary by length with a range of bend radii from 500 mm to 2000 mm. In some embodiments, the bend radius does not extend to the distal end of the nail. In some embodiments, there is a straight section of the proximal end of the nail. For example, the straight section starts at the proximal end of the nail and extends between 50 mm to 150 mm from the proximal end with a nominal value of 95 mm. In other embodiments, nail 10 may include one or more bends and/or curves that conform to the anatomical shape of the intramedullary canal.

As contemplated herein, the retrograde femoral nail or intramedullary nail may be composed of any suitable biocompatible materials. For example, the nail may be composed of titanium, cobalt chrome, cobalt-chrome-molybdenum, stainless steel, tungsten carbide, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials, or other appropriate biocompatible materials that have sufficient strength to secure and hold bone, while also having sufficient biocompatibility to be implanted into a body.

Insertion Instruments and System

In another aspect, the present invention includes a set of insertion instruments and system for advancing and positioning the retrograde femoral nail into the intramedullary canal of a femur after reaming. As further described herein, in some embodiments the femoral nail is first connected to an insertion handle and subsequently inserted into the femoral canal after reaming. In some embodiments, the insertion handle allows the surgeon to advance, retract, or rotate the nail. In some embodiments, the insertion handle is also used as a connection point for an aiming guide. In some embodiments, the insertion handle has two locating pin holes and a threaded insert that will be used to orient and connect the aiming guide. In some embodiments, the insertion handle assembly consists of a carbon fiber composite material for the handle grip mated to a stainless-steel shaft that protrudes from the handle grip and acts as a stop for the nail. In some embodiments, the stainless-steel shaft of the insertion handle has orientation tabs to correctly position the nail relative to the insertion handle. In some embodiments, the shaft of the insertion handle also includes grooves spaced at 5 mm increments to show the surgeon the location of the end of the nail under fluoroscopy. In some embodiments, the insertion handle shaft has a flanged end that seats into a pocket in the insertion handle grip. In some embodiments, the insertion handle shaft is secured in the grip by a stainless-steel pin. In some embodiments, the insertion handle shaft has an internal thread that retains the connection bolt that is used to connect the nail to the insertion handle.

In some embodiments, the aiming guide is constructed of a composite carbon fiber material and is used to target the holes in the intramedullary nail to allow the surgeon to insert locking screws without fluoroscopy and associated radiation. In some embodiments, the aiming guide has targeting holes with trajectories designed to intersect with the holes in the nail. In some embodiments, the targeting holes contain an off-center pin that is used to retain the driver sleeves. The off-center pin deflects when the driver sleeve is rotated to hold its position in the aiming arm. The driver sleeve is thus retained in the aiming guide to prevent it from slipping out or moving out of position. In some embodiments, the aiming guide also contains a hole to accept and guide a locking washer holder intended to hold a locking washer in position to align with the holes in the nail.

Figure 3:
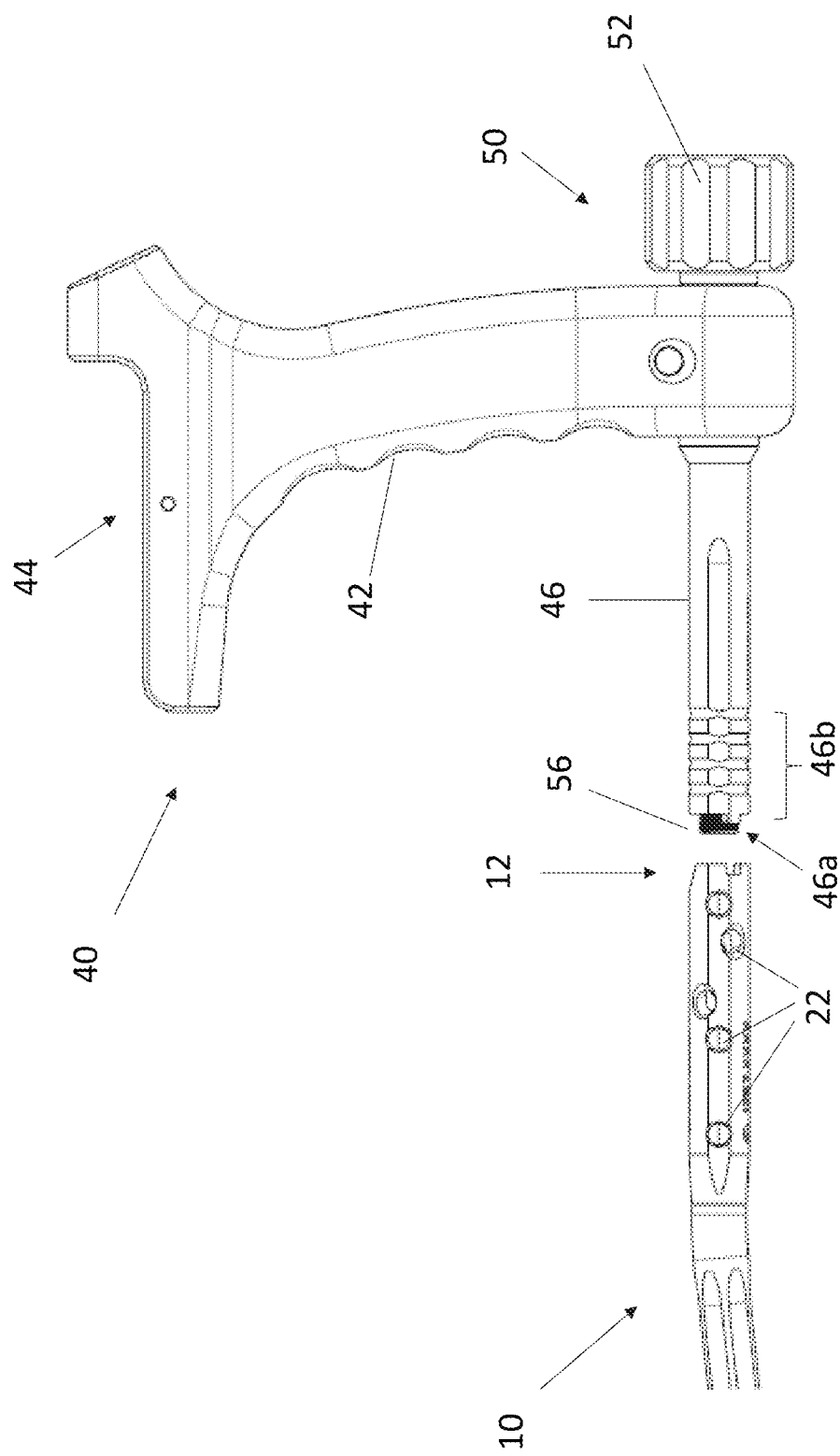
FIG. 3 illustrates an exemplary insertion handle assembly engageable with an intramedullary nail.
Figure 4:
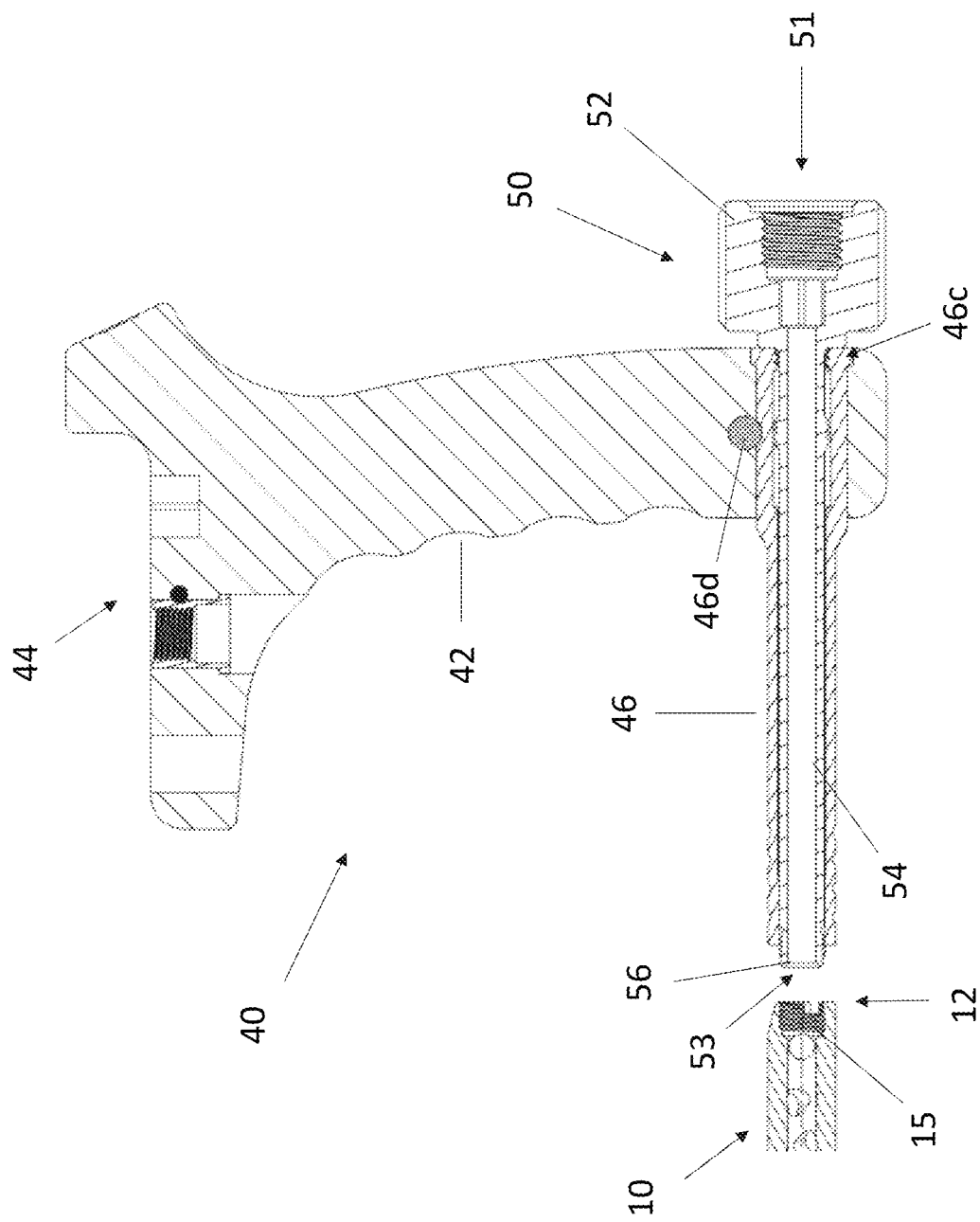
FIG. 4 is a cross-sectional view of an exemplary insertion handle assembly engageable with an intramedullary nail.

Referring now to FIGS. 3 and 4, the system includes an insertion handle 40. Handle 40 includes a grasping region 42, an aiming guide engagement region 44, a handle extension shaft 46 extending from a lower portion of grasping region 42, and a connection bolt 50. Handle extension shaft 46 has a channel having a distal opening from the back surface of the grasping region 42 through to a proximal opening at the proximal end of handle extension shaft 46. Connection bolt 50 includes an impaction cap 52, a bolt shaft 54 with proximal end threading 56 at the proximal end of shaft 54.

In some embodiments, the insertion handle 40 is made of a carbon fiber composite material for the handle grip and the handle extension shaft 46 is made of a stainless-steel that protrudes from the handle grip and acts as a stop for the nail. It should be appreciated that the insertion handle and extension shaft may each be made from any suitable material described herein. In some embodiments, extension shaft 46 includes orientation tabs 46a to correctly position the nail relative to the insertion handle. In some embodiments, the shaft 46 also includes grooves 46b spaced at about 5 mm increments to show the surgeon the location of the end of the nail under fluoroscopy. In some embodiments, the shaft 46 has a flanged end 46c that seats into a pocket in the insertion handle grip. In some embodiments, the shaft 46 is secured in the grip by a stainless-steel pin 46d.

Figure 5:
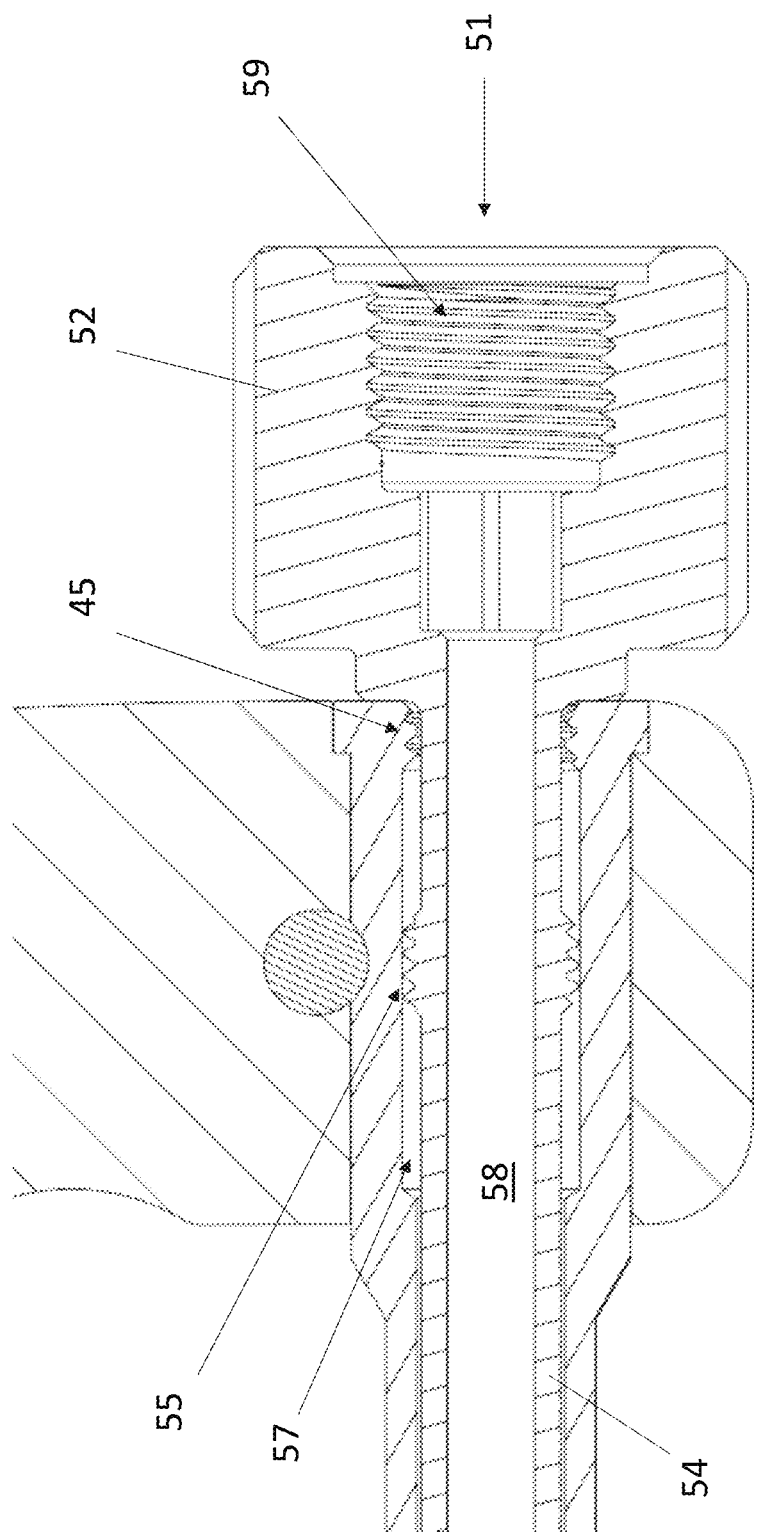
FIG. 5 is a close-up cross-sectional view of an exemplary insertion handle assembly.

Referring also to FIG. 5, connection bolt 50 is positioned and retained within the channel of handle extension shaft 46, such that connection bolt shaft 54 passes through both the lower end of grasping region 42 and handle extension shaft 46 with proximal end threading 56 being extendible beyond the proximal end of extension shaft 46. In some embodiments, connection bolt shaft 54 may include distal threads 55 along a portion of its length which are configured to engage threading 45 in the distal opening of the handle extension shaft. The proximal region of connection bolt 50 is passed through the channel of handle extension shaft 46 until threads 55 engage threading 45. Proximal to threading 45, a portion of the channel within handle extension shaft 46 is undercut to form a slightly enlarged retention region or cavity 57 of the channel. Retention region 57 permits the portion of bolt shaft 54 containing distal threads 55 to move axially and rotate therein after passing beyond threads 45, but does not permit distal threads 55 to move proximally beyond retention region 57, thereby retaining connection bolt 50 within handle extension shaft 46.

Figure 6:
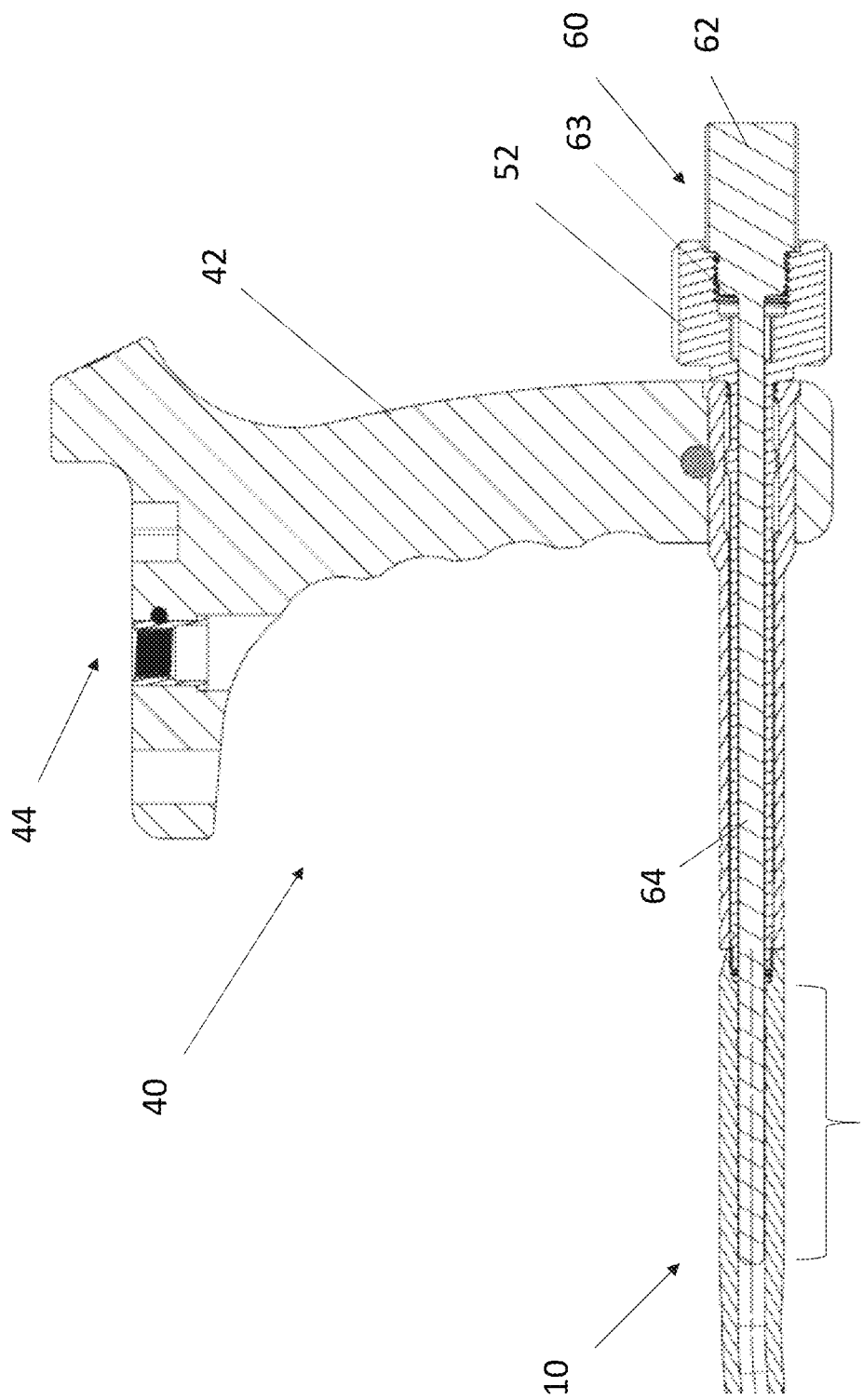
FIG. 6 is another cross-sectional view of an exemplary insertion handle assembly engageable with an intramedullary nail.
Figure 7:
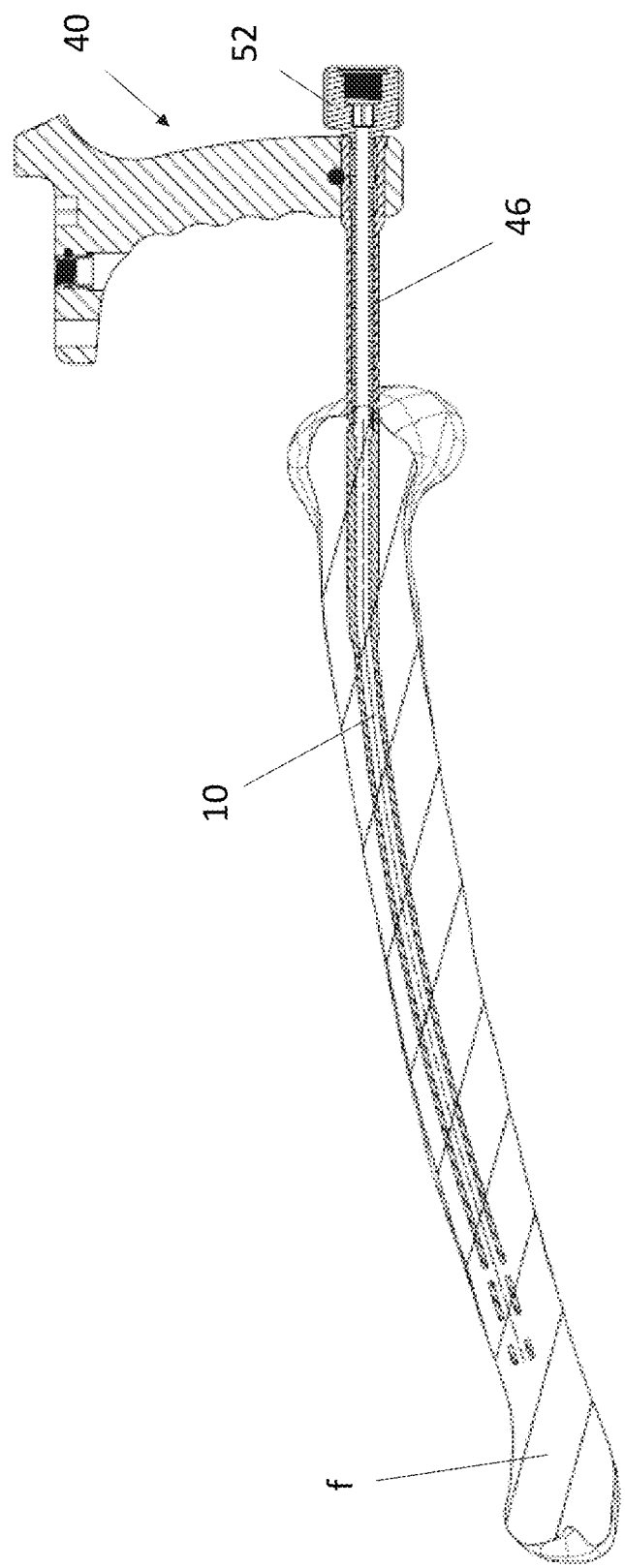
FIG. 7 is a cross-sectional view of an exemplary insertion handle assembly engaged with an intramedullary nail and inserted into bone.

Connection bolt 50 further includes a longitudinal channel 58 through its entire length, having a distal opening 51 (having threading 59) and a proximal opening 53. As shown in FIGS. 5 and 6, An assembly shaft 60 is sized and shaped for insertion in channel 58 of connection bolt 50. Assembly shaft 60 includes a shaft head 62 with threads 63 at the proximal end of shaft head 62 for engaging threading 59 of distal opening 51 of connection bolt 50. Assembly shaft 60 also includes an extension shaft 64, extending proximally from shaft head 62. Assembly extension shaft 64 is sized to pass through and protrude from proximal opening 53 of connection bolt 50 when threads 63 of assembly shaft 60 are engaged with threading 59 of connection bolt 50. The proximal region of assembly extension shaft 64 protruding from proximal opening 53 of connection bolt 50 may be a nail engagement region 65 configured to fit or within distal cannulation 13 of nail 10 (or otherwise engage the distal end or region of nail 10) to help align the nail and other component parts of the system. As contemplated herein, the assembly shaft 64 may utillize a clearance fit into the cannulation of the nail. It may be used to pilot the nail and help the user align the orientation tabs 46a with the slots in the nail. In some embodiments the insertion instruments engage the retrograde femoral nail in multiple ways. For example, the opening of distal end 12 of nail 10 may be threaded 15 and engage proximal end threads 56 of connection bolt 50 to secure the nail to the insertion tool in the desired position. Further, when the assembly shaft 60 is inserted into connection bolt 50, nail engagement region 65 inserts into distal cannulation 13 of nail 10 for aligning the nail as desired. Accordingly, as shown in FIG. 7, nail 10 is inserted into a femur f through a retrograde approach via the insertion instruments described herein.

Figure 8B:
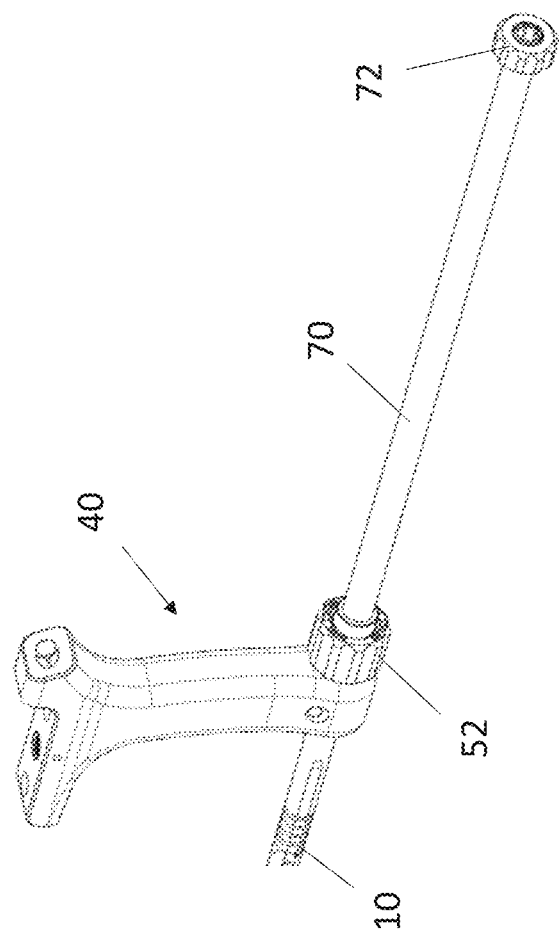
FIGS. 8A and 8B illustrate an exemplary back slap shaft attachable to the insertion handle assembly.
Figure 8A:
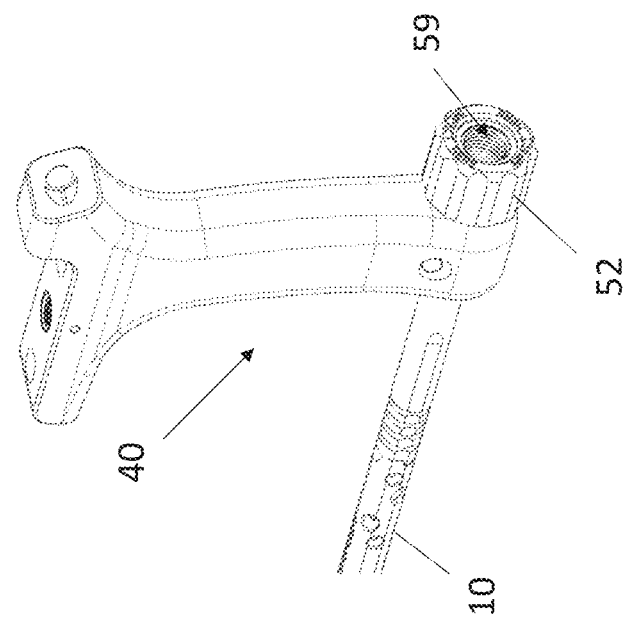

As mentioned previously, impaction cap 52 includes a threaded opening 59 for engagement with assembly shaft 60. In some embodiments and as shown in FIGS. 8A and 8B, threaded opening 59 may also be configured to engage the threaded end of a back slap shaft 70 with a fixed end knob 72. A slotted mallet or back slap hammer can slidably engage back slap shaft 70 to impact end knob 72 to retract an intramedullary nail or other implanted fixation device.

In another aspect and as shown in FIGS. 9A and 9B, the insertion instrumentation and system further includes an aiming guide 90. In some embodiments, aiming guide 90 includes a central connecting arm 91 and two flanking arcuate guide arms 92. As contemplated herein, aiming guide 90 sets the trajectory of the fasteners (e.g., locking screws, anchors, etc) to interface with one or more distal openings 22 of the nail 10.

In some embodiments, aiming guide 90 is made from a composite carbon fiber material and is used to target the holes in the intramedullary nail to allow the surgeon to insert locking screws without fluoroscopy and associated radiation. In some embodiments, aiming guide 90 is made of a radiolucent material. It should be appreciated that aiming guide 90 may be made from any other materials as described herein.

Connecting arm 91 is configured to releasably engage and/or lock into engagement region 44 of insertion handle 40. Any engagement mechanism suitable for releasable securement may be used. For example, in some embodiments, a knob 94 connected to a threaded post 94a may be used to releasably secure aiming arm 90 to insertion handle 40. Connecting arm 91 may further include one or more locating pins or dowels 93 to promote proper positioning and fitting into engagement region 44. It should be appreciated that engagement region 44 of handle 40 may include any reciprocal mating feature necessary for attachment and securement of aiming guide 90 to insertion handle 40. FIG. 9A shows aiming guide 90 prior to engagement with insertion handle 40, while FIG. 9B shows aiming guide 90 secured to insertion handle 40.

Each arcuate guide arm 92 includes one or more upper guide regions 95 and one or more lower guide regions 96. Within each guide region is one or more guide holes 97 and/or 98. Guide holes 97 and 98 may each align with a respective distal opening 22 of nail 10. In some embodiments, one or more guide holes 97 and 98 do not align with a distal opening 22.

Figure 10B:
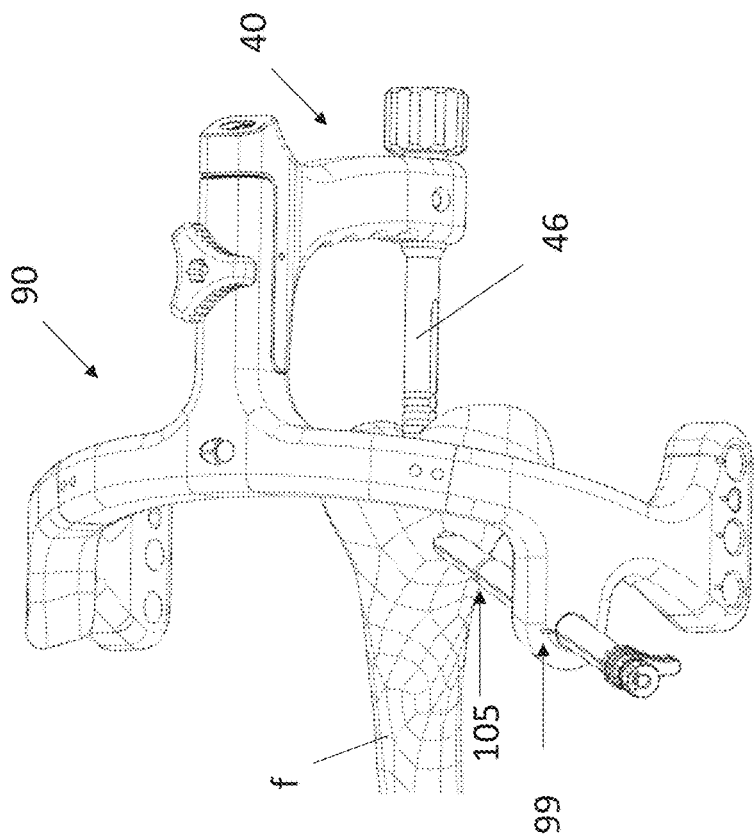
FIGS. 10A and 10B illustrate an exemplary driver sleeve in isolation and inserted into the aiming guide.
Figure 10A:
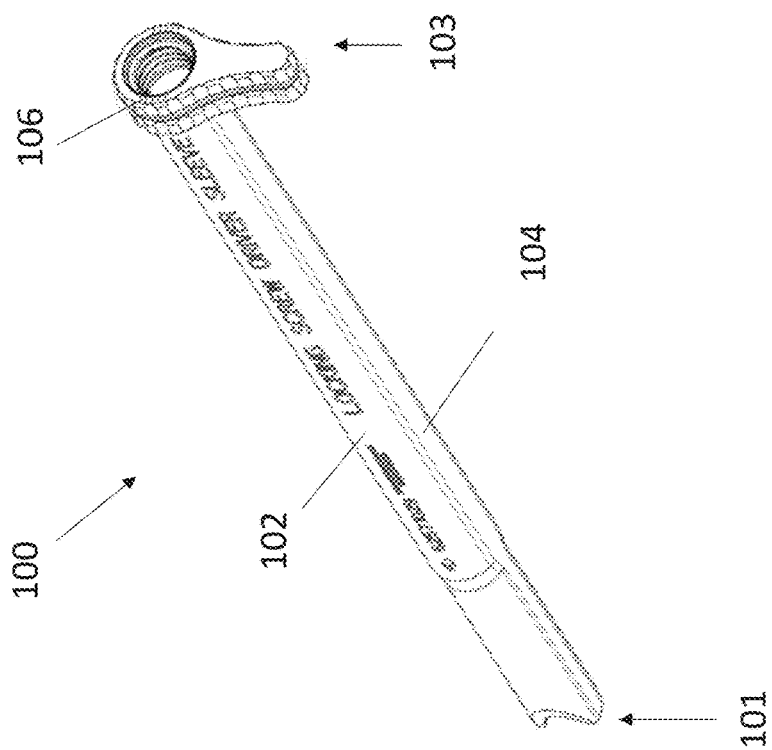

One or more guide holes 97 and 98 are sized to receive a driver sleeve 100 therethrough. Guide holes 97 and 98 may be any shape, such as circular, oval, slotted and the like. Driver sleeves 100 are used to protect the soft tissue during the drilling process of a surgical procedure. Driver sleeves 100 are hollow and are sized to accept all types of drill sleeves and trocars of various sizes. In some embodiments and as shown in FIG. 10, driver sleeve 100 includes a hollow shaft 102 having a distal end 103 with a knob 106 and a proximal end 101. Shaft 102 may be of any desired cross-sectional shape suitable for insertion into guide holes 97 and 98 of aiming guide 90. For example, driver sleeve 100 may have a generally round or oval cross-sectional shape. In some embodiments, driver sleeve 100 may have a flattened surface region 104 that runs longitudinally along a part or all of the length of shaft 102. Further, driver sleeve 100 may include an alignment marker 105 on the opposing outer surface from flattened surface region 104, or otherwise about 180° radially about the circumference from flattened region 104 of shaft 102. In other embodiments, alignment marker 105 can be placed on any desired location of driver sleeve 100. Guide holes 97 and 98 may include an alignment marker 99 which can be lined up with driver sleeve marker 105 to assist in proper alignment of driver sleeve 100 during insertion.

Figure 11C:
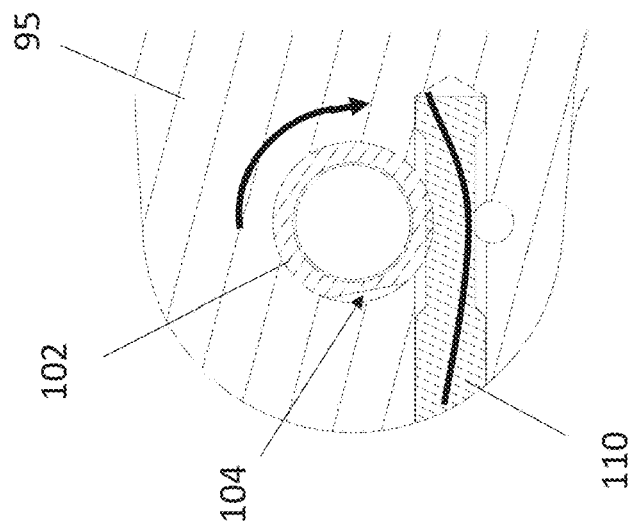
FIGS. 11A-11C are cross-sectional views of an exemplary sleeve or shaft retention mechanism.
Figure 11B:
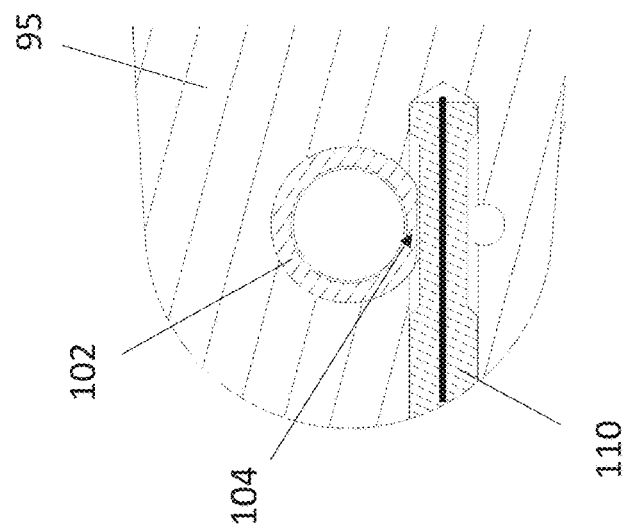
Figure 11A:
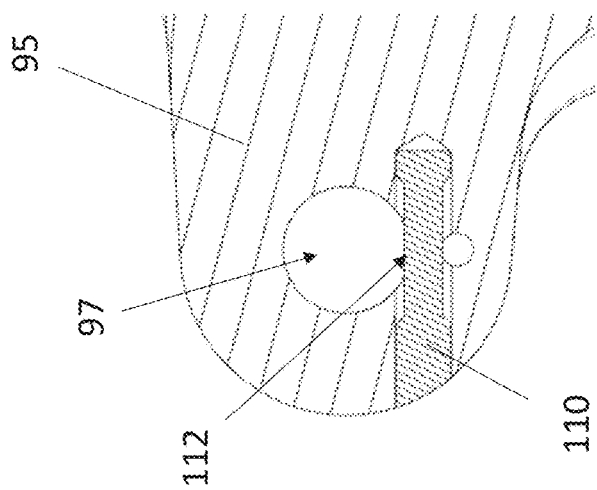

In some embodiments, aiming guide 90 includes a retention mechanism for securing driver sleeve 100 into place after insertion through a guide hole 97 or 98. For example and as shown in FIGS. 11A-11C, guide region 95 of aiming guide 90 includes a guide hole 97. A retention pin 110 may be at least partially or fully embedded into guide region 95 such that at least a portion of the surface 112 of retention pin 110 is exposed to the opening of guide hole 97. In some embodiments, the exposed surface 112 of retention pin 110 may protrude into the opening of guide hole 97. The proximal end of driver sleeve 100 is then inserted through guide hole 97 using alignment markers 99 and 105, such that flattened surface region 104 of driver sleeve 100 is facing the exposed surface 112 of retention pin 110. This configuration (shown in FIG. 11B) represents the smallest outer diameter of hollow shaft 102 at a perpendicular angle to retention pin 110. Using knob 106 to rotate driver sleeve 100 (in a clockwise manner as shown in FIG. 11C), the flattened surface region 104 moves off of retention pin 110, such that the largest outer diameter of hollow shaft 102 is at a perpendicular angle to retention pin 110. This results in a downward force of hollow shaft 102 into retention pin 110 (i.e. retention pin 110 deflection), thereby creating a frictional securement of driver sleeve 100 within guide hole 97. In other embodiments, pin 110 may be replaced with other structures, such as a spring biased structure or any other mechanism that provides a temporary frictional securement of driver sleeve 100 within a guiding hole of aiming guide 90.

Figure 12B:
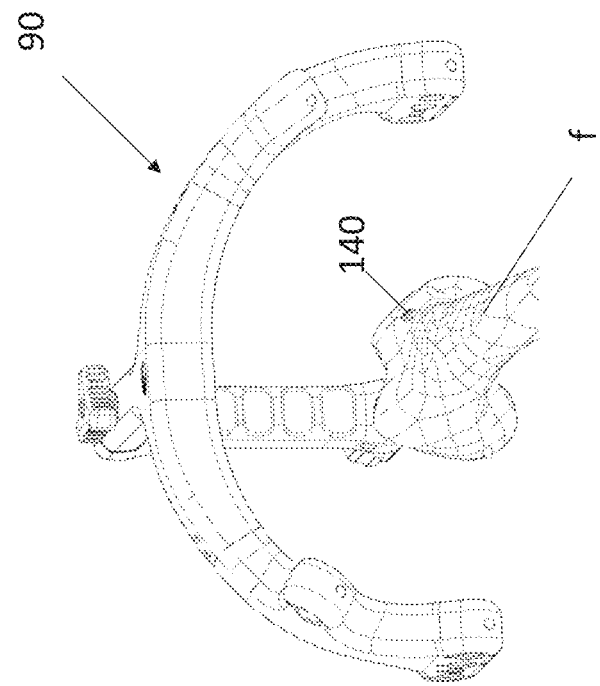
FIGS. 12A and 12B illustrate an exemplary placement of a locking screw into an intramedullary nail within bone.
Figure 12A:
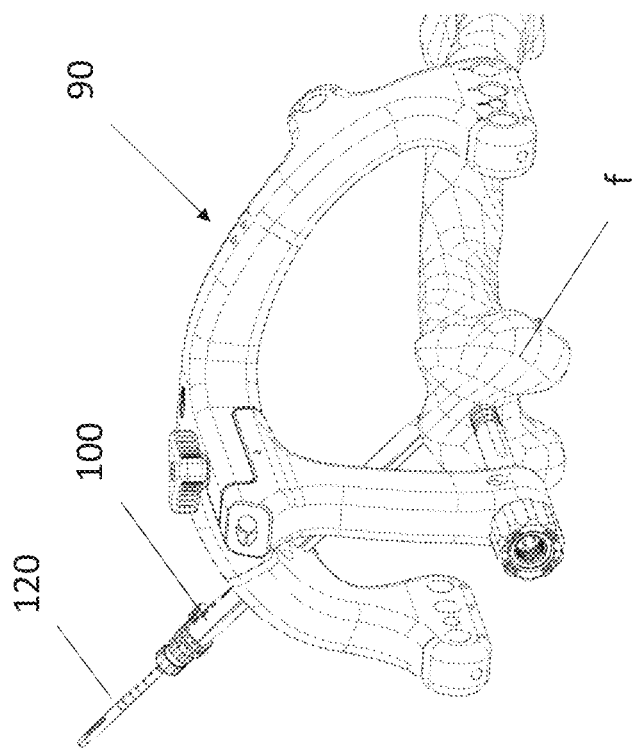
Figure 13B:
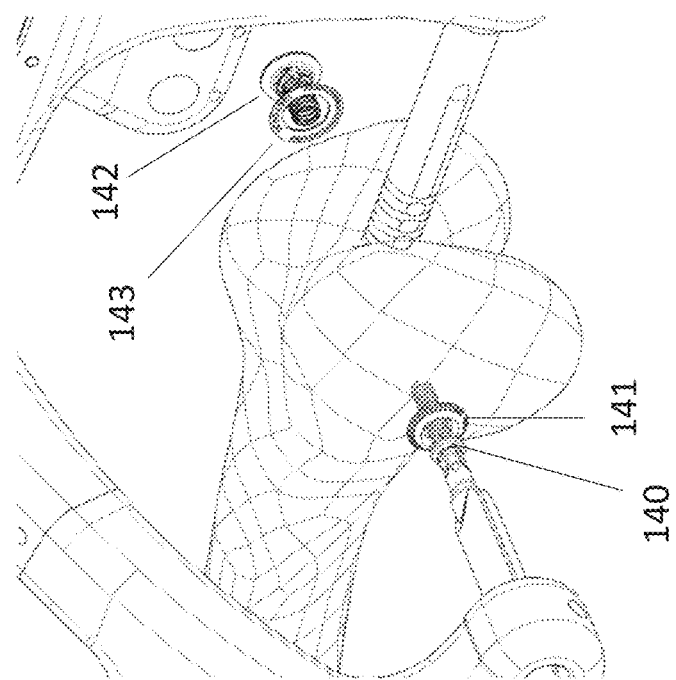
Figure 13A:
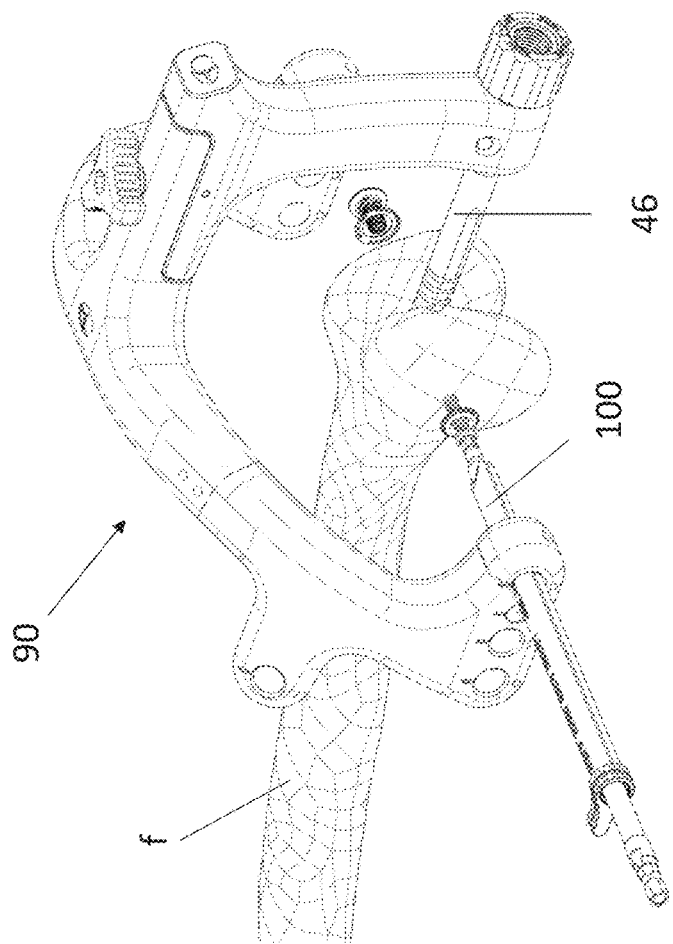

Upon securement of driver sleeve 100 and as shown in FIG. 12A, a drill 120 may be inserted through the hollow opening of driver sleeve 100 and the target region of the bone drilled. The drill is then withdrawn from driver sleeve 100 and a locking screw 140 is inserted and driven into the bone f and through the correspondingly aligned distal opening 22 of nail 10. Locking screw 140 is shown fully inserted into the bone and nail in FIG. 12B, with the driver sleeve removed.

Further implementation of the aforementioned femoral nail and insertion instrumentation will now be shown and described across FIGS. 13A-13E. For example, condyle washers 141, nuts 142, and nut washers 143 may be used with locking screws 140 to compress the femoral condyles. The washers 141 and 143 may be used to distribute the compressive load generated by the locking screws 140 to the condyles. As shown in FIGS. 13A-13E, a first driver 145a is used to thread locking screw 140 into a corresponding distal opening 22 of nail 10 and a second driver 145b is used to thread a condyle nut 142 onto locking screw 140 from the opposite side. Locking screw 140 is rotated via driver 145a to apply compression to one side. After appropriate compression is achieved on the first side, locking screw 140 is held in place by driver 145a as condyle nut 142 and a washer 143 are rotated via driver 145b to advance over the threads of locking screw 140 on the other side. Condyle nut 142 and washer 143 are advanced until appropriate compression is achieved.

Figure 14B:
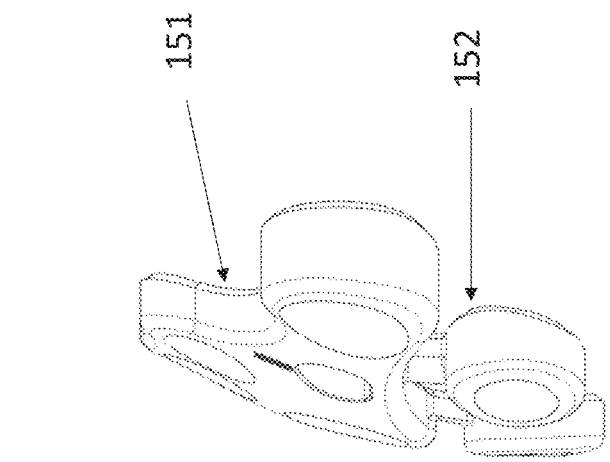
FIGS. 14A and 14B illustrate an exemplary locking washer.
Figure 14A:
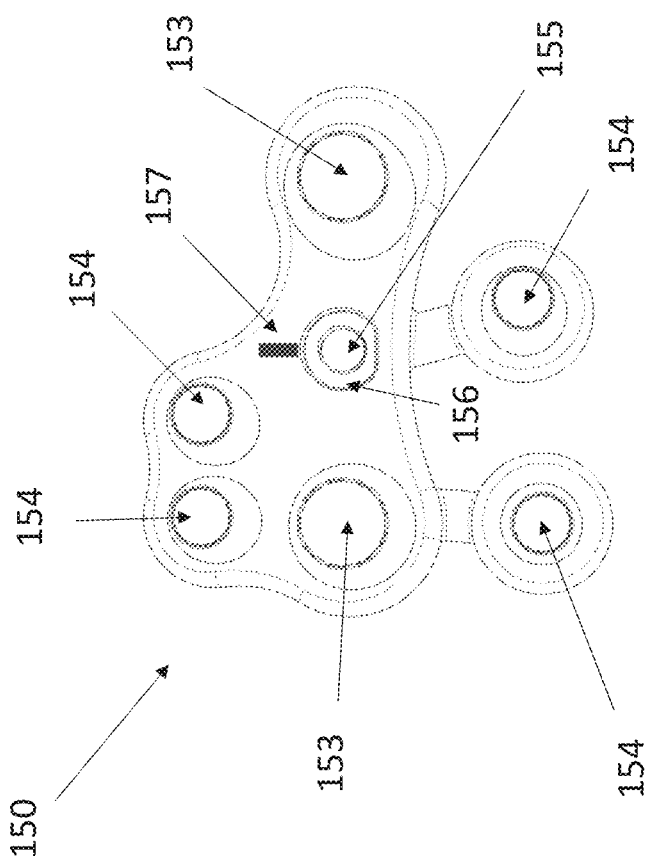

In some embodiments, a multi-hole locking washer is included to augment fixation in the femoral condyles. For example, as shown in FIGS. 14A and 14B, a locking washer 150 may include a precontoured portion 151 and/or a deformable portion 152, such as deformable tabs or hinging regions of locking washer 150. Locking washer 150 may further include one or more types of polyaxial locking holes, such as 5.0 polyaxial locking holes 153 and/or 3.5 polyaxial locking holes 154. One or more threaded mounting holes 155 may also be included. There is no limitation to the number of holes or the orientation of holes within locking washer 150, other than one or more of holes 153 should correspondingly align with the trajectory from guiding holes 97 and 98 of aiming guide 90 to distal openings 22 of nail 10. A locking washer alignment marker 157 may be included for aligning the locking washer 150 with driver sleeve 100 or any other holder 160 or placement tool. The locking washer 150 may be made from stainless steel or titanium or alloy thereof, or any other suitably sturdy material described herein.

Figure 15B:
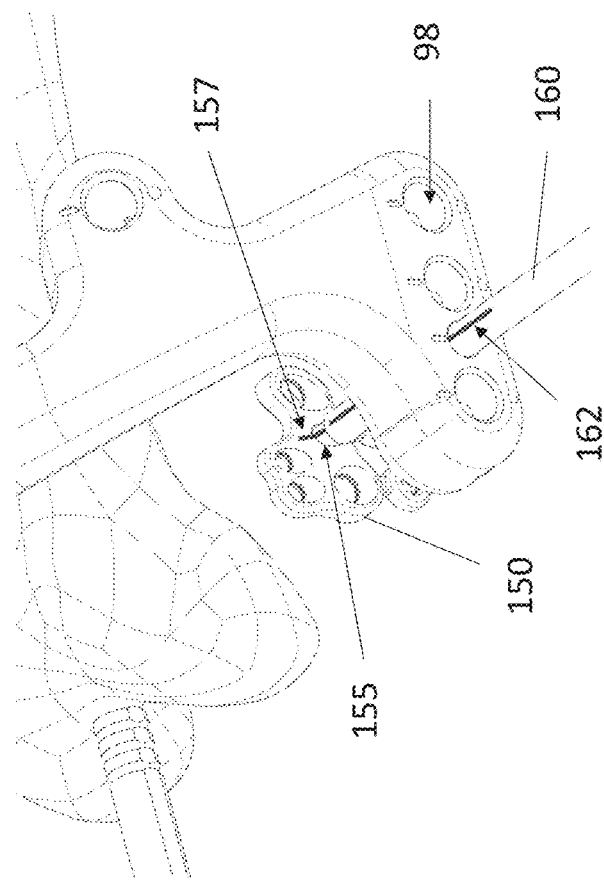
FIGS. 15A and 15B illustrate an exemplary engagement of a locking washer with a locking washer holder.
Figure 15A:
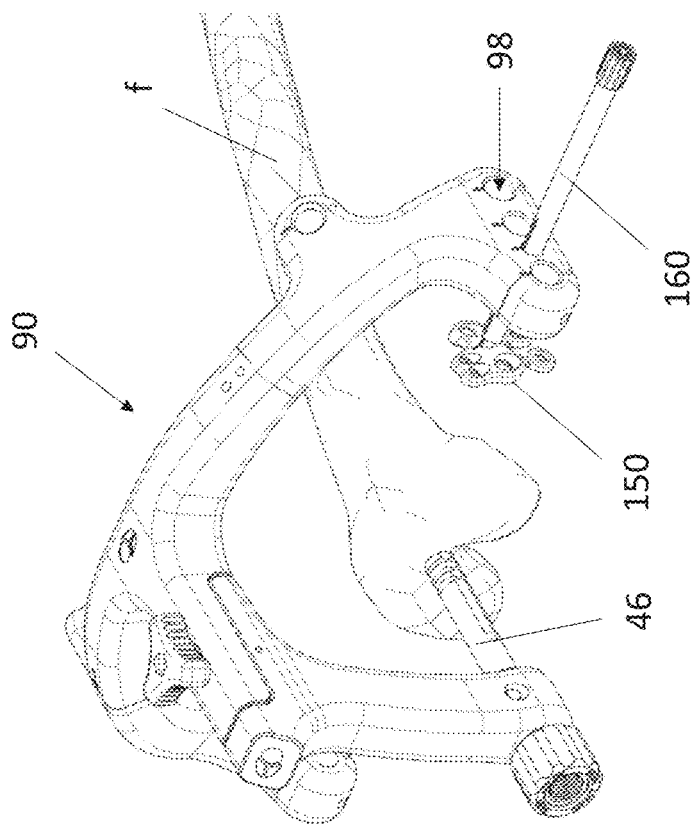

In some embodiments, locking washer 150 may be unitized with nail 10 through two 5.0 polyaxial locking holes 153. Locking washer 150 may also utilize four 3.5 polyaxial locking holes 154 for additional fixation strength. In some embodiments, the trajectories of 3.5 locking holes 154 are intended not to intersect with distal openings 22 of nail 10. As shown in FIGS. 15A and 15B, threaded mounting hole 155 may further include an alignment pocket 156 to connect to a holder instrument 160 used to position and hold the locking washer prior to fixing with screws. Washer holder 160 may include an alignment marker 162 at its proximal end, which may be used to align with marker 157 of locking washer 150 to assist in proper placement of locking washer 150 against bone. In some embodiments, locking washer 150 may only engage holder 160 in a single orientation due to a specific fit with the geometry of alignment pocket 156 of mounting hole 155. In some embodiments, locking washer 150 may be precontoured 151 to match the anatomy of the lateral femur. In some embodiments, locking washer 150 may have deformable tabs 152 that can be bent in-situ for optimum fit.

Figure 16B:
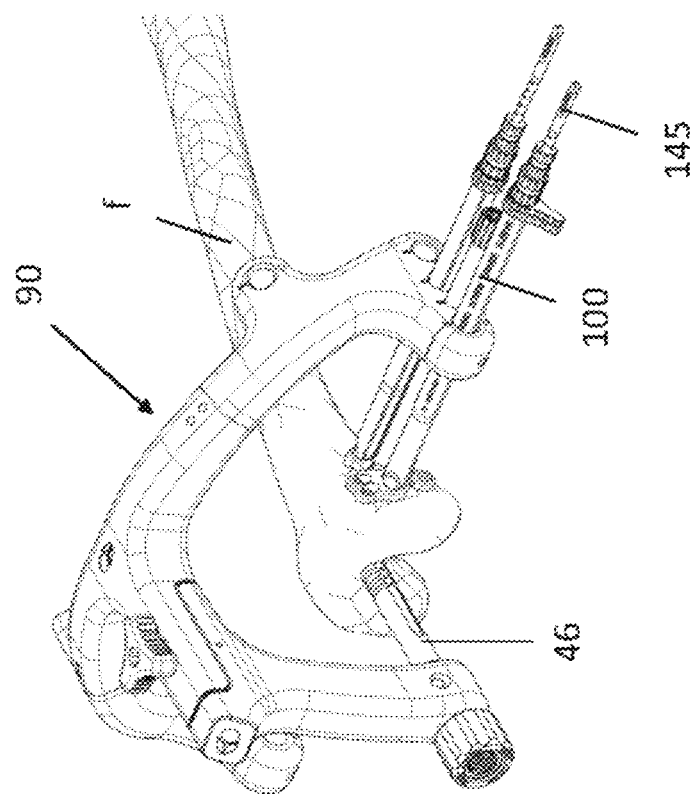
FIGS. 16A and 16B illustrate an exemplary securement of a locking washer to the intramedullary nail within bone.
Figure 16A:
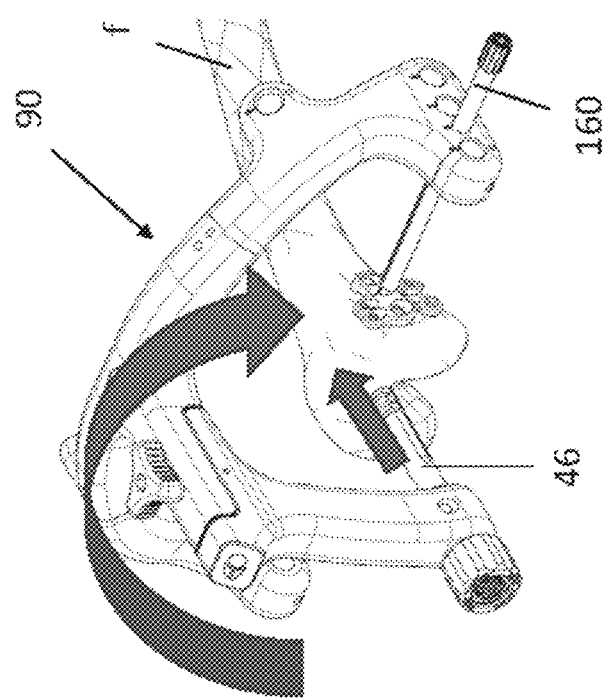
Figure 17B:
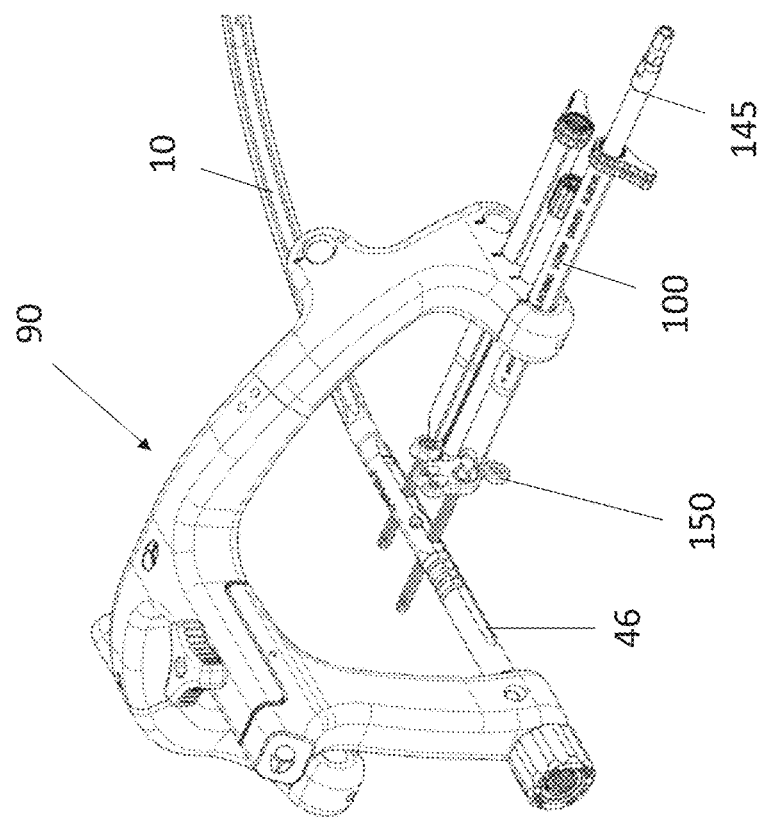
FIGS. 17A and 17B illustrate the secured locking washer with and without bone.
Figure 17A:
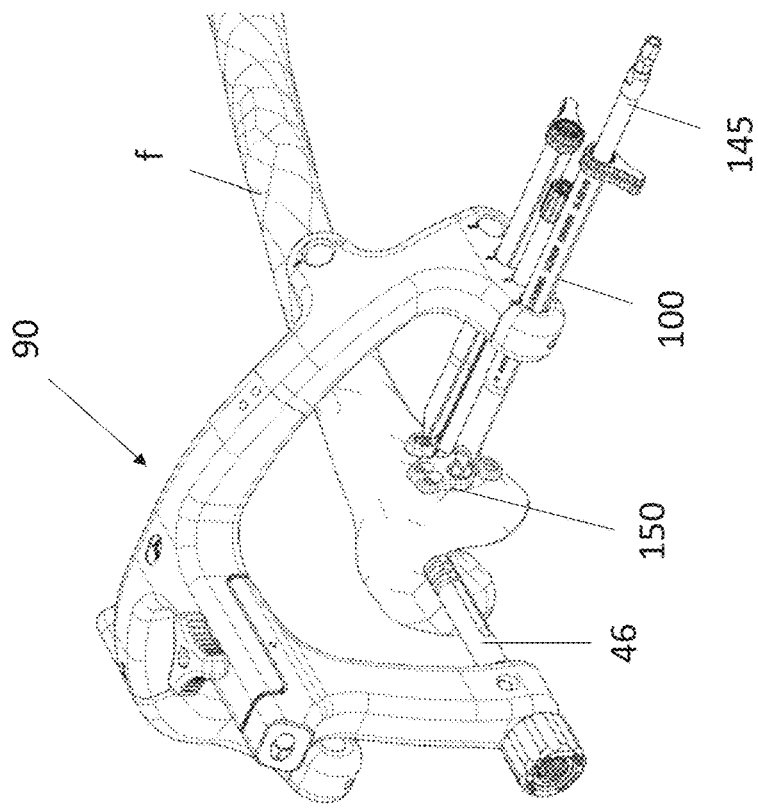
Figure 18B:
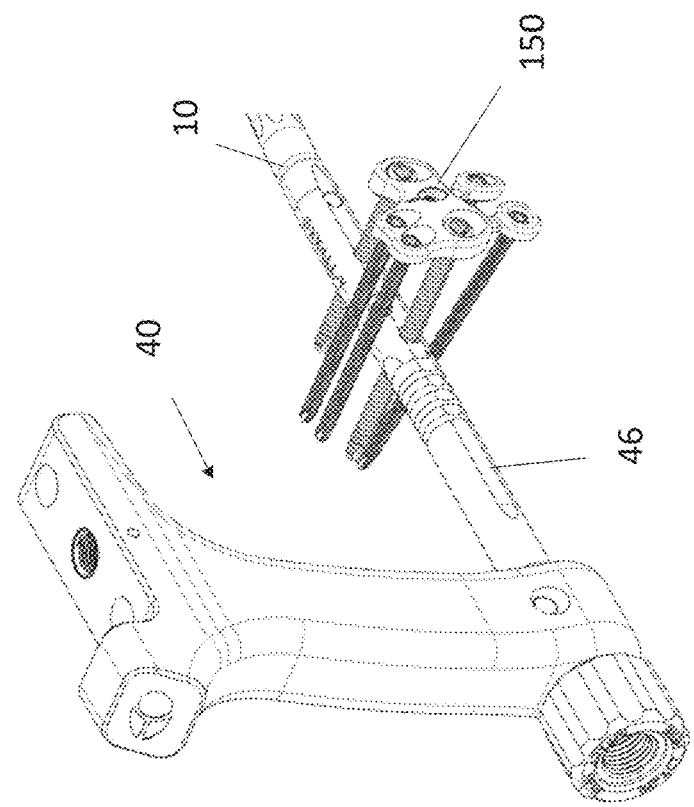
FIGS. 18A and 18B illustrate the secured locking washer with the aiming guide removed, both with and without bone.
Figure 18A:
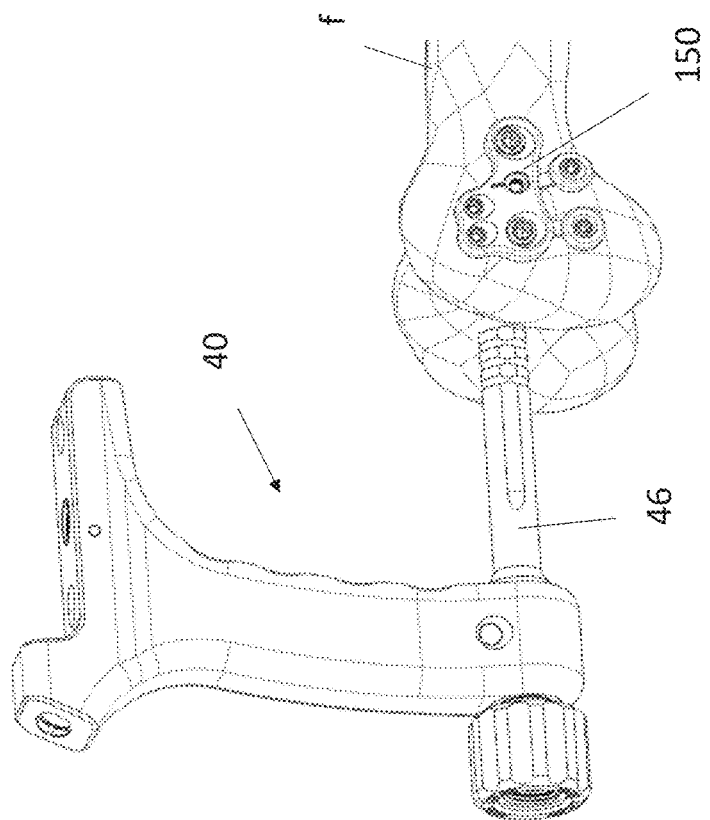

In some embodiments and as shown in FIG. 16A, the entire insertion instrument assembly can be rotated and/or advanced to obtain ideal washer fitment. For example, locking washer 150, nail 10, insertion handle 40, and aiming guide 90 may all move together to find the ideal fit on the target bone. As shown in FIG. 16B, once locking washer 150 is positioned, a drill 145 may be advanced through driver sleeve 100 to secure the 5.0 locking screws through locking washer 150, bone f, and nail 10. The secured 5.0 locking screws are shown with bone and without bone in FIGS. 17A and 17B, respectively. In some embodiments, all driver sleeves 100 and washer holders 160 can be removed from aiming guide 90, and aiming guide 90 may also be removed from insertion handle 40 prior to inserting 3.5 locking screws, which do not engage nail 10 and therefore do not utilize or necessarily require the aiming guide assembly for proper alignment. FIGS. 18A and 18B show locking washer 150 with secured 5.0 and 3.0 locking screws both with bone and without bone, respectively. FIGS. 19A and 19B show the final construct with all insertion instrumentation removed, both with and without bone, respectively.

The disclosures of any patent, patent application, and/or publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An intramedullary nail system, comprising:
   an intramedullary nail comprising:
      an elongate body having a distal end, a proximal end and a length therebetween;
      a cannulation from the distal end into a distal region of the elongate body, wherein an opening at the distal end of the cannulation is threaded;
      a first set of threaded transverse openings each passing through the elongate body in the distal region, wherein at least one of the threaded transverse openings is a four-start threaded opening; and
      a second set of transverse openings passing through the elongate body in a proximal region of the elongate body
   an insertion handle configured to couple to the intramedullary nail and coupled to an aiming guide, wherein the aiming guide includes a plurality of guiding holes;
   a locking washer, the locking washer having a plurality of openings; and
   a plurality of locking screws,
   wherein at least one of the plurality of guiding holes of the aiming arm aligns with at least one of the openings in the locking washer and the at least one of the openings in the locking washer aligns with at least one of the openings in the first or the second set of threaded transverse openings in the elongate body of the intramedullary nail such that at least one of the plurality of locking screws can be inserted through the guiding hole of the aiming arm and engage with the locking washer and the intramedullary nail.

2. The nail of claim 1, wherein at least one of the first set of threaded transverse openings is positioned 54 mm from the distal end of the elongate body.

3. The nail of claim 2, wherein at least one of the first set of threaded transverse openings is positioned 8 mm from the distal end of the elongate body.

4. The nail of claim 1, wherein at least one of the first set of threaded transverse openings is at an oblique angle from a longitudinal axis of the elongate body.

5. The nail of claim 4, wherein the oblique angle opening is configured to have a trajectory towards a posterior condyle of a femur when the nail is positioned within the intramedullary canal of the femur.

6. The nail of claim 1, wherein the nail has a proximal bend of 5° to 10°.

7. The nail of claim 6, wherein the nail has a radius of curvature extending to the proximal end of the elongate body.

8. The nail of claim 7, wherein the proximal bend begins proximally from the distal region of the elongate body.

9. The nail of claim 1, wherein the distal region of the elongate body has a larger cross-sectional diameter than the remainder of the elongate body.

10. The nail of claim 1, wherein the second set of transverse openings includes one slotted opening and three threaded openings.

11. An intramedullary nail insertion system, comprising:
an insertion handle having a front surface and a back surface;
a hollow extension shaft having a threaded distal end opening and a proximal end opening, the distal end initiating from the back surface of the handle and the proximal end extending outward from the front surface of the insertion handle, thereby forming a channel from the back surface of the handle to the proximal end of the extension shaft;
wherein the extension shaft channel includes a cavity portion proximal to the distal threaded end opening;
a hollow connection bolt having a distal end and a threaded proximal end and a length therebetween, wherein the hollow connection bolt is sized to fit within the hollow extension shaft, and wherein the hollow connection bolt includes a threaded region on an outside surface along a length and sized to engage the threaded distal end opening of the hollow extension shaft;
wherein the cavity portion of the extension shaft has a diameter equal to or greater than the outer diameter of the threaded proximal end of the hollow connection bolt, and wherein the portion of the channel of the hollow extension shaft proximal to the cavity has a diameter that is smaller than the outer diameter of the threaded proximal end of the hollow connection bolt; and
an aiming guide having two opposing arcuate guide arms and a connection arm, wherein the connection arm releasably engages the insertion handle, and wherein each guiding arm includes one or more guide holes;
a driver sleeve sized to fit within the one or more guide holes of the aiming guide;
a driver sleeve retention mechanism, wherein the mechanism is configured to generate a frictional securement of the driver sleeve when the driver sleeve is inserted into the guide hole of the aiming guide and rotated radially;
an insertion assembly shaft having a distal end and a proximal end and a length therebetween, wherein the assembly shaft length fits within a hollow interior of the connection bolt, and wherein the length of the insertion assembly shaft is greater than the length of the hollow connection bolt, such that the proximal end of the assembly shaft is extendable into a distal end cannulation of the intramedullary nail when the nail is engaged with the connection bolt; and
a locking washer having one or more holes that align with both the one or more guide holes of the aiming guide and the one or more distal end openings of the intramedullary nail,
wherein one or more of the guide holes of the aiming guide are aligned with one or more distal end openings of the intramedullary nail when the nail is engaged with the connection bolt,
wherein the threaded proximal end of the hollow connection bolt extends beyond the proximal end of the hollow extension shaft and is sized to engage and secure a threaded distal end of an intramedullary nail.

12. The insertion system of claim 11, wherein the aiming guide includes a washer mounting guide hole, and wherein the locking washer includes a mounting hole aligned with the washer mounting guide hole of the aiming guide.

13. The insertion system of claim 11, wherein the locking washer includes a precontoured region configured to match the surface of a target bone.

14. The insertion system of claim 11, wherein the locking washer includes a deformable region, wherein at least one hole is positioned within the deformable region.

* * * * *